United States Patent [19]

Holt et al.

[11] Patent Number: 4,946,834

[45] Date of Patent: Aug. 7, 1990

[54] PHOSPHONIC ACID SUBSTITUTED STEROIDS AS STEROID 5α-REDUCTASE INHIBITORS

[75] Inventors: Dennis A. Holt, Downingtown; Mark A. Levy, Wayne; Brian W. Metcalf, Radnor, all of Pa.

[73] Assignee: SmithKline Beecham Corporation, Philadelphia, Pa.

[21] Appl. No.: 290,211

[22] Filed: Dec. 23, 1988

[51] Int. Cl.$^5$ .................... A61K 31/66; C07J 1/00; C07J 43/00
[52] U.S. Cl. ..................... 514/119; 514/75; 514/120; 514/130; 514/134; 424/601; 540/23; 540/95; 540/100; 540/5; 552/506; 552/611; 552/505; 552/607; 552/609; 552/599; 552/603; 552/636; 552/640; 552/633; 552/539; 552/610
[58] Field of Search ............... 424/601; 540/23, 95, 540/100, 5; 260/397, 397.5; 514/75, 119, 120, 130, 134

[56] References Cited

U.S. PATENT DOCUMENTS

| | | | |
|---|---|---|---|
| 4,191,759 | 3/1980 | Johnston et al. | 260/397.1 |
| 4,317,817 | 3/1982 | Blohm et al. | 260/397.5 |
| 4,361,578 | 11/1982 | Alig et al. | 549/331 |
| 4,377,584 | 3/1983 | Rasmusson et al. | 546/77 |

OTHER PUBLICATIONS

Hsia and Voight, J. Invest. Dermat., 62:224–227 (1973).
Robaire et al., J. Steroid Biochem., 8:307–310 (1977).
Blohm, T. R., et al., Biochem. Biophys. Res. Comm. 95:273–280 (1980).
Liang, T., et al., J. Steriod Biochm. 19, 385–390 (1983).
Petrow, V., et al., Steroids 38:121–140 (1981).
Brooks et al., Steroids: 47:1–19 (Jan. 1986).

*Primary Examiner*—Joseph A. Lipovsky
*Attorney, Agent, or Firm*—Wayne J. Dustman; Stuart R. Suter; Edward T. Lentz

[57] ABSTRACT

Invented are substituted acrylate analogues of steroidal synthetic compounds, pharmaceutical compositions containing the compounds, and methods of using these compounds to inhibit steroid 5α-reductase. Also invented are intermediates used in preparing these compounds.

24 Claims, No Drawings

PHOSPHONIC ACID SUBSTITUTED STEROIDS AS STEROID 5α-REDUCTASE INHIBITORS

FIELD OF THE INVENTION

The present invention relates to steroid-3-phosphonic acid compounds, pharmaceutical compositions containing these compounds, and methods for using these compounds to inhibit mammalian steroid 5α-reductase.

DESCRIPTION OF RELATED ART

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, acne vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5α-reduced androgens are the active hormones in some tissues such as the prostate and sebaceous gland. Circulating testosterone thus serves as a prohormone for dihydrotestosterone (DHT), its 5α-reduced analogue in these tissues but not in others such as muscle and testis. Steroid 5α-reductase is a NADPH-dependent enzyme that converts testosterone to DHT. The importance of this enzyme in male development was dramatically underscored by discovery of a genetic steroid 5α-reductase deficiency in male pseudohermaphrodites. Imperato McGinley, J., et al., (1979), *J. Steroid Biochem.* 11: 637-648.

Recognition of the importance of elevated DHT levels in many disease states has stimulated many efforts to synthesize inhibitors of this enzyme. The structures of several known steroid 5α-reductase inhibitors are shown in Table 1.

TABLE 1

| | 5α-Reductase Inhibitors | | |
|---|---|---|---|
| COMPOUND | | $K_I$ | REFERENCE |
| (1) | COOH | $1.1 \times 10^{-6}$ M (Reversible) | Hsia and Voight 1973 |
| (2) | | $1 \times 10^{-6}$ M (Irreversible) | Robaire, et al. 1977 |
| (3) | OH | $3.5 \times 10^{-8}$ (Irreversible) | Blohm, et al., 1980 |
| (4) | | $5 \times 10^{-9}$ M (Reversible) | Liang, et al, 1983 |

TABLE 1-continued

| 5α-Reductase Inhibitors | | | |
|---|---|---|---|
| COMPOUND | | $K_I$ | REFERENCE |
| (5) | 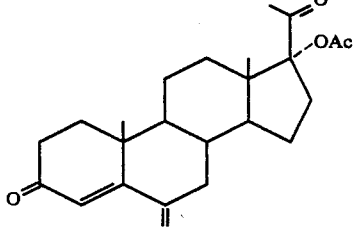 | $1.25 \times 10^{-6}$ M (Irreversible) | Petrow, et al., 1981 |

The first inhibitor described was the 17-β-carboxylic acid (1) by Hsia and Voight in 1973. *J. Invest. Dermat.* 62:224–227. The secosteroid (2) was the next inhibitor to be described and also has found utility as an affinity label for 5α-reductase. Robaire, B., et. al., (1977), *J. Steroid Biochem.* 8:307–310. The diazoketone (3) has been reported as a potent, time-dependent inhibitor of steroid 5α-reductase. Blohm, T. R., et. al. (1980), *Biochem. Biophys. Res. Comm.* 95:273–280; U.S. Pat. No. 4,317,817, Mar. 2, 1982. Compound (4) is exemplary of a group of 4-aza steroid inhibitors of steroid 5α-reductase described in U.S. Pat. No. 4,377,584 which issued Mar. 22, 1983, and in Liang, T., et al. (1983), *J. Steroid Biochem.* 19, 385–390. The 6-methylene steroid (5) also has been shown to be a time dependent inactivator of steroid 5α-reductase. Petrow, V., et. al. (1981), *Steroids* 38:121–140.

Other steroid 5α-reductase inhibitors also have been described. U.S. Pat. No. 4,361,578 which issued June 2, 1986, describes a class of homosteroid enzyme inhibitors. U.S. Pat. No. 4,191,759 discloses amides of 17β-carboxy-4-androsten-3-one that are active as steroid 5α-reductase inhibitors. Japanese Patent Nos. J6014685-5A and J60116657-A disclose various aniline derivatives having numerous activities including 5α-reductase inhibiting activity. Japanese Patent No. J60142941-A discloses phenyl substituted ketones having 5α-reductase inhibiting activity and European Patent No. EP173516-A discloses various phenyl substituted amides having similar activity. Shiseido referenced terpene derivatives that are active inhibitors of steroid 5α-reductase. Japanese Patent No. J59053417-A.

Preparation of a diethyl steroidal-3-phosphonate, in which the A ring is an aryl ring, has been reported Petrakis et al., *J. Am. Chem. Soc.* 109:2831-2833(1987).

SUMMARY OF THE INVENTION

The present invention resides in the discovery that steroid 5α-reductase is inhibited by certain steroidal-3-phosphonic acid compounds. The A ring in these compounds is a non aromatic ring. The compounds are potent enzyme inhibitors.

Presently preferred compounds of the invention and compounds used in the invented pharmaceutical compositions and the invented methods include:
17β-(N,N-diisopropylcarboxamide)-androst 3,5 diene 3 phosphonic acid,
17β-(N-t-butylcarboxamide)-androst-3,5-diane-3-phosphonic acid,
17β-(N,N-diisopropylcarboxamide)5α-androst-3-ene-3-phosphonic acid,
17β-(N,N-diisopropylcarboxamide)5α-androst-2-ene-3-phosphonic acid, and
17β-(N,N-diisopropylcarboxamide)-androst-2,4-diene-3-phosphonic acid.

Other compounds of the invention include, but are not limited to, the following:
20α-(hydroxymethyl)-5α-pregn-3-ene-3-phosphonic acid,
17β-(N,N-diisopropylcarboxamide)-4-fluoro-5α-androst-3-ene-3-phosphonic acid,
20α-(hydroxymethyl)-4-fluoro-5α-pregn-3-ene-3-phosphonic acid,
20α-(hydroxymethyl)-A-nor-5α-pregn-1-ene-2-phosphonic acid,
17β-(N,N-diisopropylcarboxamide)-5α-androst-1,3-diene-3-phosphonic acid,
17β-(N,N-Diisopropylcarboxamide)-5α-androstane-3β-phosphonic acid,
17β-(N,N-Diisopropylcarboxamide)-estr-3,5(10)-diene-3-phosphonic acid,
17β-(N,N-Diisopropylcarboxamide)-estr-3,5-diene-3,5-diene-3-phosphonic acid,
17β-(N,N-Diisopropylcarboxamide)-androst-3,5,11-triene-3-phosphonic acid, and
17β-(N-t-Butylcarboxamide)-androst-3,5,11-triene-3-phosphonic acid.

In a further aspect of the invention there are provided novel processes useful in preparing the presently invented 5α-reductase inhibiting compounds and novel $C_{1-8}$ alkyl phosphonate esters which are useful as intermediates in preparing the phosphonic acids of this invention and are also useful as prodrugs. Exemplary of the esters is monomethyl 17β-(N,N-diisopropylcarboxamide)-androst-3,5-diene-3-phosphonate.

The invention also relates to a method for inhibiting 5α-reductase activity in mammals, including humans, that comprises administering to a subject in need thereof an effective amount of a presently invented 5α-reductase inhibiting compound.

Included in the present invention are pharmaceutical compositions comprising a pharmaceutical carrier and compounds useful in the methods of the invention.

DETAILED DESCRIPTION OF THE INVENTION

The phosphonic acid compounds of this invention that inhibit steroid 5α-reductase have the following Formula (I):

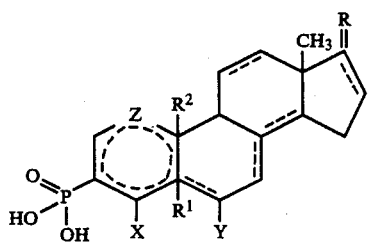

in which:

The A ring has up to 2 double bonds;

The B, C, and D rings have optional double bonds where indicated by the broken lines, provided that the A, B, C rings do not have adjacent double bonds and the D ring does not have a $C_{16}$-$C_{17}$ double bond when R represents two substituents or a divalent substituent;

Z is $(CH_2)_n$ and n is 0–2;

X is H, Cl, F, Br, I, $CF_3$, or $C_{1-6}$ alkyl;

Y is H, $CF_3$, F, Cl or $CH_3$, provided that Y is H when there is no $C_5$-$C_6$ double bond;

$R^1$ is absent or present as an alpha hydrogen provided $R^1$ is absent when there is a $C_4$-$C_5$, $C_5$-$C_6$, or $C_5$-$C_{10}$ double bond; and $R^2$ is absent or present as H or $CH_3$, provided $R^2$ is absent when the carbon to which it is attached is double bonded; and R is (1) α-hydrogen, α-hydroxyl, or α-acetoxy and/or

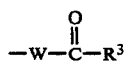

where W is a bond or $C_{1-12}$alkyl and $R^3$ is (i) hydrogen,
(ii) hydroxyl,
(iii) $C_{1-8}$alkyl,
(iv) hydrox$C_{1-8}$alkyl,
(v) $C_{1-8}$alkoxy,
(vi) $N(R^4)_2$, where each $R^4$ is independently selected from hydrogen, $C_{1-8}$-alkyl, $C_{3-6}$cycloalkyl, phenyl or taken together with the nitrogen to which they are attached represent a 5–6 membered saturated heterocylic ring comprising up to one other heteroatom selected from oxygen and nitrogen, or
(vii) $OR^5$, where $R^5$ is alkali metal, $C_{1-18}$alkyl, benzyl, or (b) Alk- $OR^6$, where Alk is $C_{1-12}$alkyl, and $R^6$ is
(i) phenyl$C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—W—CO—$R^3$ or =CH—W—$OR^6$, where W is a bond or $C_{1-12}$alkyl, and $R^3$ and $R^6$ have the same meaning as above and $R^6$ also is hydrogen or $C_{1-20}$alkylcarbonyl;

(3) 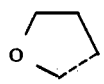

where the dashed bond replaces the 17α-hydrogen, (4) α-hydrogen and $NHCOR^7$ where $R^7$ is $C_{1-12}$alkyl or $N(R^4)_2$ where $R^4$ has the same meaning as above, (5) α-hydrogen and cyano, (6) α-hydrogen and tetrazolyl, or (7) keto;

or a pharmaceutically acceptable salt thereof.

As used herein, unless otherwise specified, $C_{1-m}$alkyl and $C_{1-m}$alk means a straight or branched hydrocarbon chain having 1 to m carbons and Alk means a straight or branched hydrocarbon chain having 1 to 12 carbons.

Preferred among Formula (I) compounds are those in which Z is —$CH_2$—.

Also, preferred among the presently invented compounds are those having Formula (II):

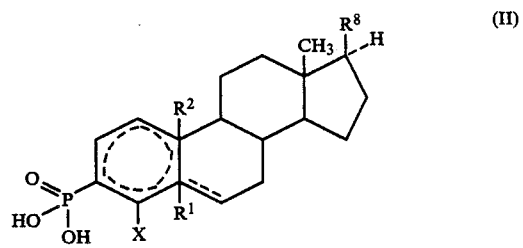

in which:

the A ring has up to 2 double bonds;

the B ring has an optional double bond where indicated by the broken line and provided that the A and B rings do not have adjacent double bonds;

X is H, or halo, and $R^1$ is absent when there is a $C_4$—$C_5$, $C_5$-$C_6$, or $C_5$-$C_{10}$ double bond, or present as an alpha hydrogen, and $R^8$ is (a) $C(CH_3)CH_2OR^9$ wherein $R^9$ is H or $C_{1-6}$alkyl, or (b) $CON(R^9)_2$ wherein each $R^9$ independently is H or $C_{1-6}$alkyl.

Particularly preferred are Formula (II) compounds in which the A ring has a $C_3$-$C_4$ double bond. Also particularly preferred are Formula (II) compounds in which $R^8$ is N,N-diisopropylcarboxamide which is —$CON(C_3H_7)_2$.

Also preferred among the presently invented compounds are those having Formula (III):

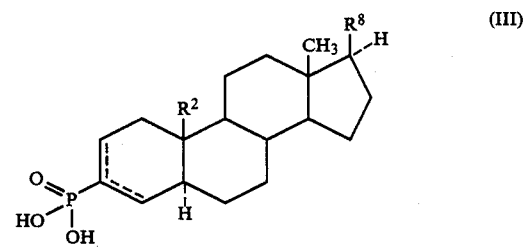

in which, $R^2$ and $R^8$, are as in Formula (II) and the A ring has one double bond.

Additionally, preferred among the presently invented compounds are those having Formula (IV):

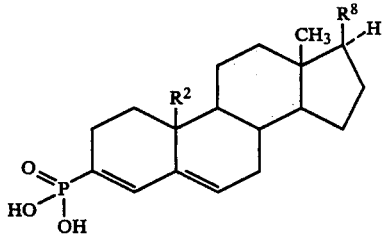
(IV)

in which $R^2$, and $R^8$ are as in Formula (II).

Compounds of Formula (I) are included in the pharmaceutical compositions of the invention and used in the methods of the invention.

Also included in this invention are the $C_{1-8}$alkyl phosphonates of the formula:

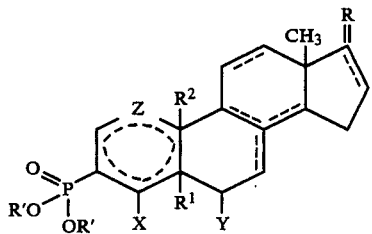
(Ia)

in which: one R' is $C_{1-8}$alkyl and the other R' is hydrogen or $C_{1-8}$alkyl; and the A, B, C and D ring double bonds, Z, X, Y, R, $R^1$ and $R^2$ are as defined in Formula (I).

As used above and throughout the remainder of the specification and claims the carbons of the steriod nucleus are numbered and the rings are lettered as follows:

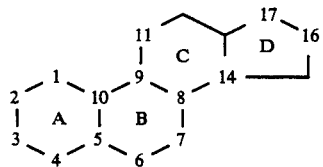

Formula (I) compounds are prepared as shown in Schemes I through IX wherein $R^2$ and X are as defined in Formula (I). $R^{10}$ is R or moieties which can be converted to those of R by known chemical reactions such as described in J. Fried and J. Edwards, *Organic Reactions in Steroid Chemistry*, Pub: Nostrand Reinhold Company (1972) provided that $R^{10}$ does not include any such moieties that render inoperative the Schemes I to IX processes. As demonstrated in the following Examples, reactions to convert $R^{10}$ to R are performed on products of the synthetic pathways of Schemes I through IX or, where appropriate or preferrable, on certain intermediates in these synthetic pathways.

SCHEME I

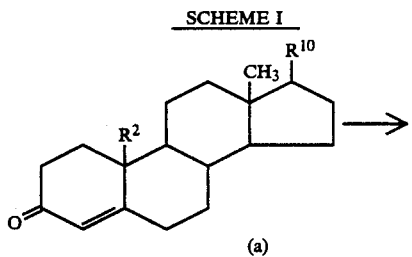
(a)

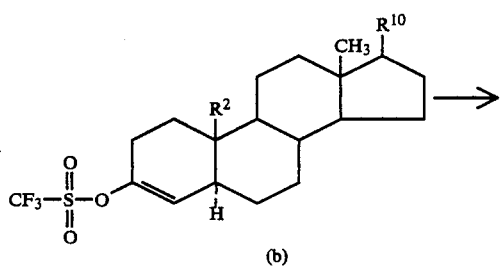
(b)

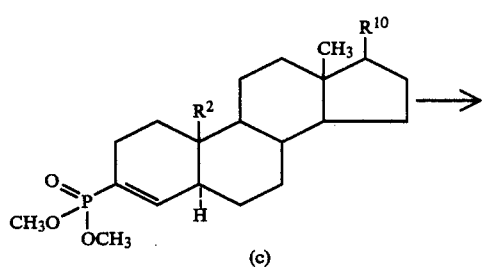
(c)

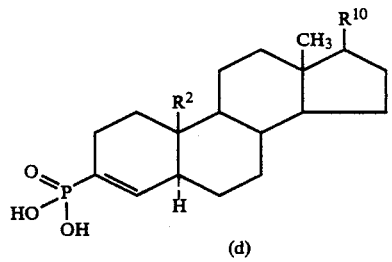
(d)

Scheme I depicts formation of Formula (I) compounds having a double bond is at $C_3-C_4$, X is H, and n is 1. The starting 4-ene-3-one compounds are known and readily available and are synthesized from available precursors using known procedures. According to Scheme I, a solution of a 4-ene-3-one compound (a) and a suitable organic proton donor such as t butanol, or, preferably aniline in an appropriate organic solvent, preferably tetrahydrofuran (THF) are added to a reducing metal amine, preferably a lithium/ammonia (Li/NH$_3$) solution, to form a reaction mixture. This reaction mixture is stirred at −100° C. to −30° C., preferably −78° C., quenched with a lithium scavenger such as dibromoethane, bromobenzene, or, preferably isoprene, and evaporated to form a residue. Formula (b) compounds then are prepared by reacting the residue dissolved in a suitable organic solvent, preferably THF, with an N aryltrihaloalkylsulfonimide, preferably N-phenyltrifluoromethylsulfonimide at a temperature of −20° C. to 20° C.

Formula (c) compounds are prepared by adding to a formula (b) compound dissolved in a suitable organic solvent such as dimethylformide (DMF) an organic base such as trimethylamine, or, preferably, triethylamine, and a phosphite such as dimethylphosphite. The solution is flushed with argon and a palladium (0) compound such as tetrakis(triphenylphosphine) palladium (0) is added. The reaction proceeds at room temparture to give the dimethyl phosphonate esters of formula (c). Other alkyl phosphonate esters are prepared using appropriate reactants. Hydrolyzing the esters, for example with trimethylsilyl iodide in acetonitride, gives the phosphonicacids of formula (d). Mono alkyl phosphonates are prepared by treating the dialkyl esters with potassium carbonate in aquenous methanol.

SCHEME II

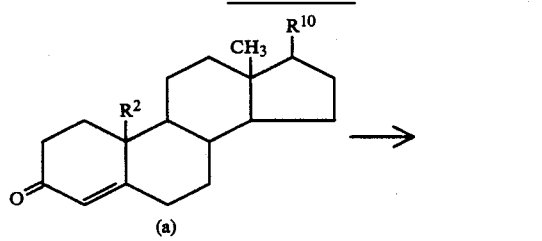
(a)

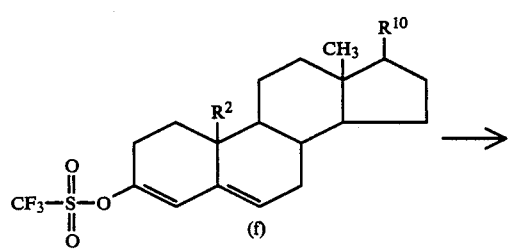
(f)

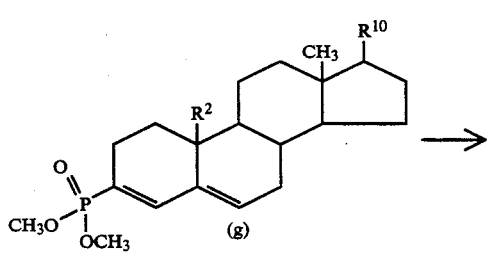
(g)

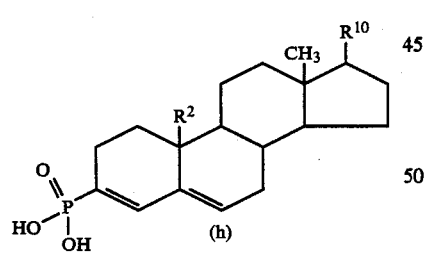
(h)

Scheme II outlines synthesis of the 3-trifluoromethylsulfonate intermediates for Formula (I) compounds wherein there is a $C_5$–$C_6$ double bond and n is 1. The starting materials are the formula (a) 4-ene-3-one compounds from Scheme 1. According to Scheme II, to a formula (a) compound dissolved in an appropriate organic solvent, preferably methylene chloride, is added 2,6-di-t-butyl-4-methylpyridine. A trihaloalkyl sulfonic anhydride, preferably trifluoromethane sulfonic anhydride then is added to yield formula (f) compounds. These intermediates are converted to dialkyl phosphonate intermediates (formula g) which are hydrolyzed to the phosphonic acid (formula h) compounds by the procedures of Scheme I (b→c→d).

SCHEME III

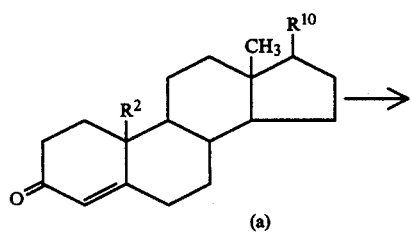
(a)

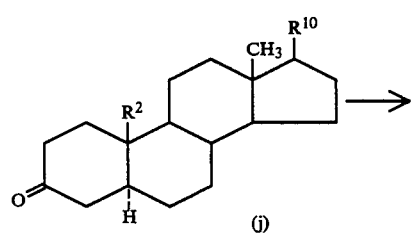
(j)

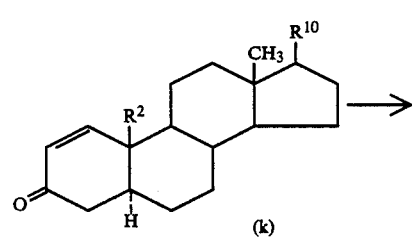
(k)

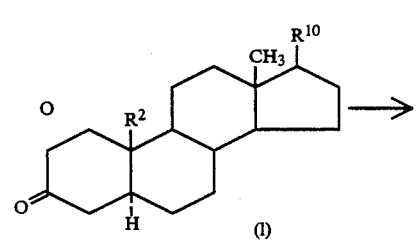
(l)

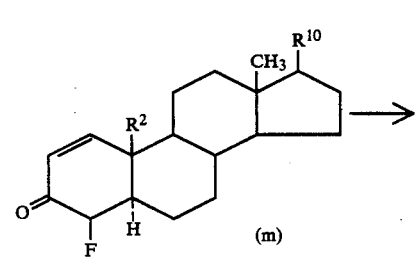
(m)

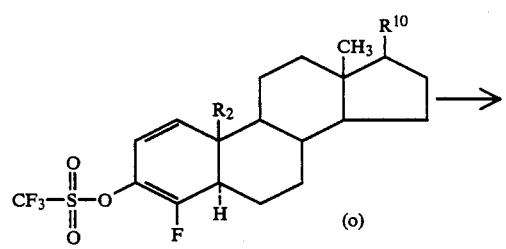
(o)

-continued
SCHEME III

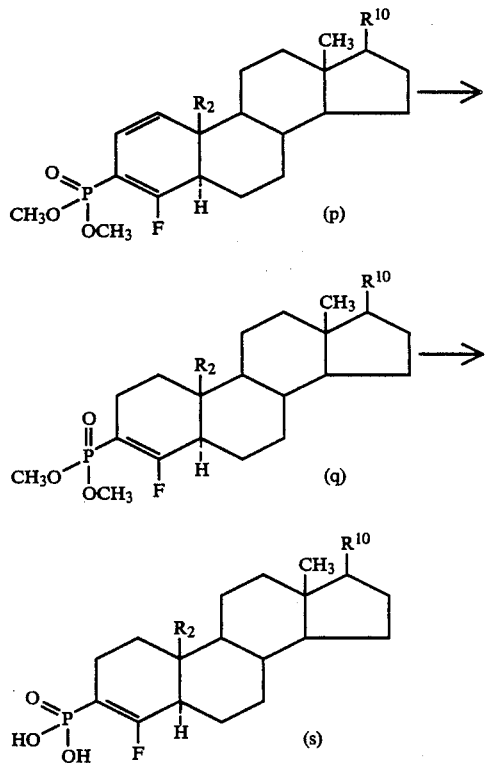

Scheme III illustrates synthesis of Formula (Ia) compounds in which X is fluoro. The starting compounds are the 4-ene-3-one compounds (a) used in Schemes I and II. According to Scheme III, formula (a) compounds dissolved in a suitable organic solvent such as THF and t-butyl alcohol are added to a metal amine solution, preferably a Li/NH$_3$ solution, to form a reaction mixture which is cooled to $-100°$ C. to $-30°$ C., preferably $-78°$ C., and quenched with a lithium scavenger agent such as dibromoethane, bromobenzene, or, preferably, isoprene to form an enolate. This enolate then is refluxed with a salt of a strong acid and base, preferably ammonium chloride (NH$_4$Cl) to yield a formula (j) compound. Addition of phenylselenyl chloride to a formula (j) compound dissolved in a suitable organic solvent, preferably ethyl acetate, followed by addition of an oxidizing agent, preferably hydrogen peroxide (H$_2$O$_2$), yields a formula (k) compound. The formula (l) epoxide compounds next are prepared by addition of an oxidizing agent, preferably H$_2$O$_2$, to a formula (k) compound dissolved in a suitable organic solvent, preferably methanol, cooled to $5°$ C. to $25°$ C., preferably $15°$ C., followed by addition of a strong base such as NaOH.

Formula (l) compounds then are dissolved in a suitable organic solvent, preferably THF, and cooled to $-20°$ C. to $0°$ C., and a fluorinating agent such as hydrogen fluoride, or, preferably, pyridinium poly(hydrogen fluoride) is added to yield formula (m) compounds. Formula (m) compounds are dissolved in a suitable organic solvent such as THF followed by addition to a solution of a metalloamide base such as lithium diisopropylamide or, preferably, lithium bis(trimethylsilyl)amide in a suitable organic solvent such as THF. To this reaction mixture then is added a triflating agent such as trifluoro methanesulfonic anhydride, or, preferably, N-phenyltrifluoromethanesulfonimide to yield formula (o) compounds.

Formula (p) compounds then are synthesized by adding to a formula (o) compound dissolved in a suitable organic solvent such as DMF an organic base such as trimethylamine, or, preferably, triethylamine; a phosphite such as dimethyl phosphite; and tetrakis(triphenylphosphine) palladium(0) to give the dimethyl phosphonate esters of formula (p). Hydrogenation of formula (p) compounds dissolved in a suitable organic solvent such as ethyl acetate and hexane using an appropriate hydrogenation agent such as platinum dioxide, Raney nickel, or, preferably palladium on carbon (Pd/carbon) yields formula (q) compounds. Hydrolysis of the ester, for example with trimethylsilyl iodide in acetonitrile, gives a formula (s) compound.

Formula (s) compounds in which X is other than hydrogen or fluoro are prepared using processes such as exemplified in Examples 23, 24, and 25.

SCHEME IV

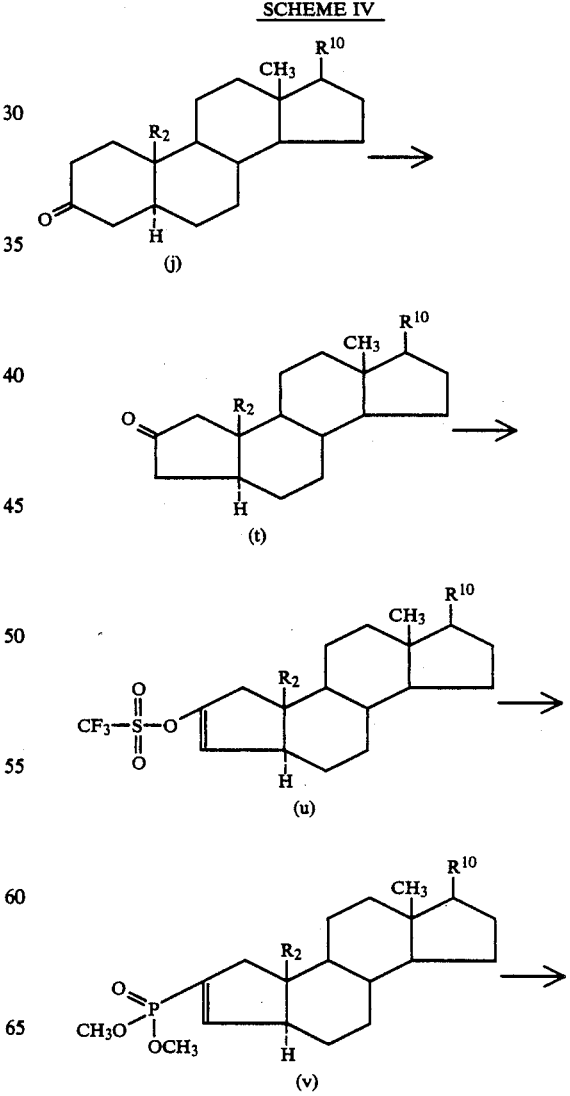

-continued
SCHEME IV

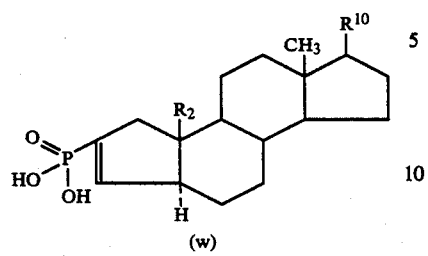

(w)

Scheme IV depicts formation of Formula (I) compounds in which n is O. The starting materials for this formation are formula (j) compounds prepared as described in Scheme III. According to Scheme IV, formula (j) compounds are dispersed in a strong acid, preferably glacial acetic acid, and treated with thallic acetate sesquihydrate to prepare a non-2-carboxylic acids which are converted to the formula (t) compounds. Formula (u) compounds next are prepared from formula (t) compounds by the procedure of Scheme III.

Formula (u) compounds are then converted to the phosphonate compounds of formula (v) by the procedure of Scheme I. The phosphonate compounds are converted to the phosphonic acids, formula (w), by the procedures of Scheme I.

SCHEME V

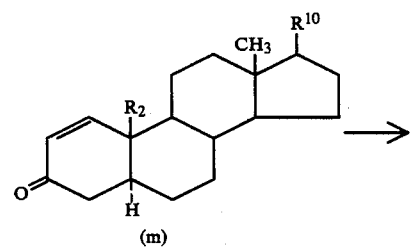

(m)

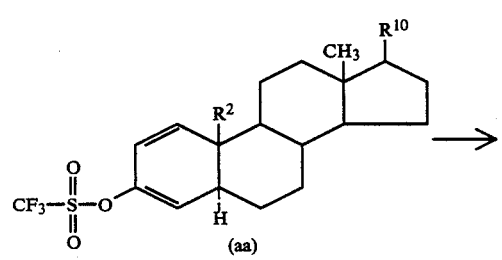

(aa)

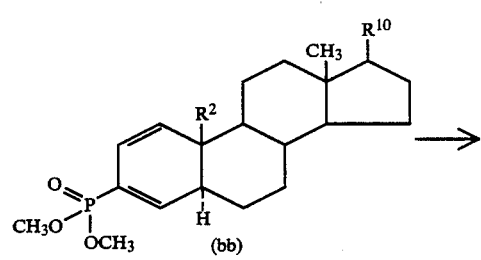

(bb)

-continued
SCHEME V

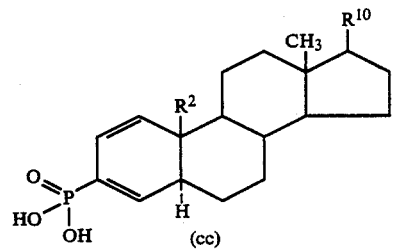

(cc)

Scheme V outlines formation of Formula (I) compounds in which $C_1$–$C_2$ and $C_3$–$C_4$ double bonds exist. The starting materials in Scheme v are Formula (I) compounds prepared as described in Scheme III. According to Scheme V, formula (aa) compounds are prepared using the processes used in making formula (f) compounds of Scheme II. The formula (aa) compounds are converted to the phosphonate esters (formula bb) and the phosphonic acids (formula cc) by the procedures described in Scheme I.

SCHEME VI

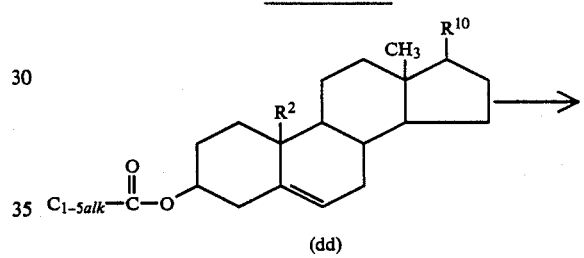

(dd)

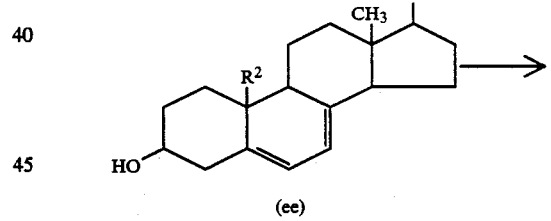

(ee)

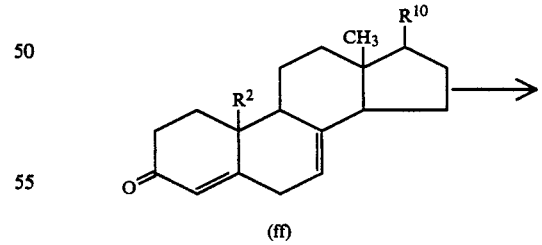

(ff)

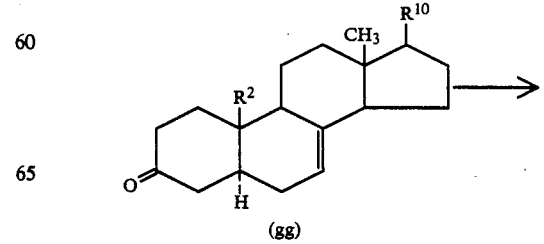

(gg)

-continued
SCHEME VI

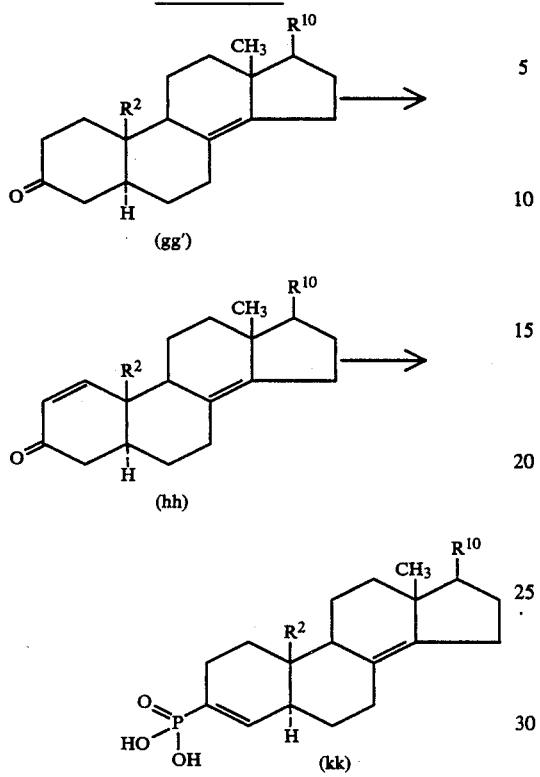

Scheme VI shows synthesis of Formula (Ia) compounds in which there is a $C_8$–$C_{14}$ double bond. The formula (dd) starting materials are known and available and can be synthesized from available materials using known methods Formula (ee) compounds are prepared by first treating formula (dd) compounds in a suitable organic solvent such as hexane with a brominating agent such as N-bromosuccinamide, or, preferably dibromantin and a mild base, preferably sodium bicarbonate, and heated, preferably at reflux. Thereafter, the mixture is treated with lithium bromide (LiBr), cooled to $-20°$ C. to $20°$ C., preferably $0°$ C., and treated with triethylamine and benzenethiol. Treatment with an oxidazing agent such as sodium periodate, hydrogen peroxide, or preferably m chloroperbenzoic acid follows and is followed by heating to $40°$ C. to $100°$ C., preferably $70°$ C., and treatment with an organic base such as trimethylamine, or preferably triethylamine. Treatment with a strong base such as sodium hydroxide, potassium hydroxide, lithium hydroxide, or, preferably, potassium carbonate yields formula (ee) compounds.

Formula (ee) compounds then are dissolved in a suitable organic solvent, preferably toluene, and treated with an alkyl ketone agent such as a cyclohexanone, or, preferably butanone followed by treatment with aluminum isopropoxide and heating, preferably at reflux, to prepare formula (ff) compounds. Reaction of formula (ff) compounds as described in forming Scheme III, formula (j) compounds yields formula (gg') compounds. Hydroqenation of formula (gg) compounds using suitable catalysts such as platinum dioxide, Raney nickel, or, preferably Pd/carbon, yields formula (gg') compound dissolved in a suitable organic solvent, preferabley ethyl acetate, followed by addition of an oxidizing agent, preferably $H_2O_2$. Substitution of formula (hh) compounds for formula (m) compounds in Scheme III yields the dimethyl phosphonate and the phosphonic acid compounds of formula (kk).

SCHEME VII

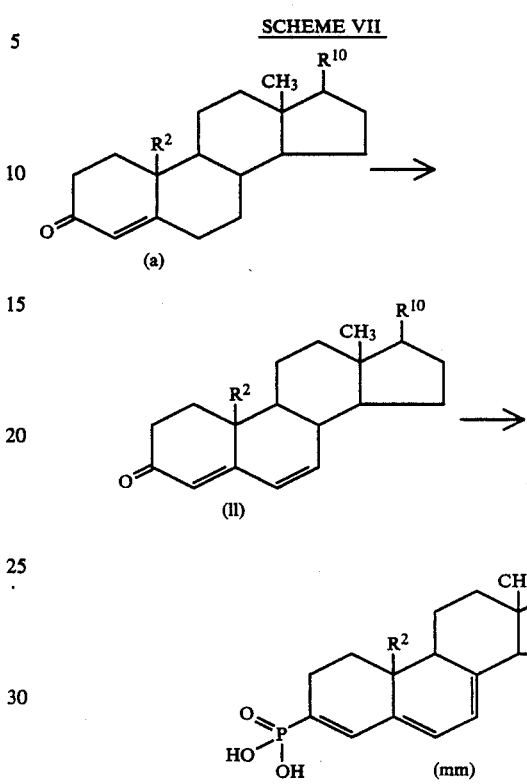

Scheme VII outlines formation of Formula (I) compounds in which a double bond exists at positions 5,6 and 7,8. These compounds are prepared using Scheme I, formula (a) compounds as starting material. Treatment of formula (a) compounds in a suitable solvent such as t-butanol with chloranil, with heating, preferably at reflux, yields formula (11) compounds. Thereafter, substituting formula (II) compounds for formula (a) compounds in the Scheme II process yields dimethyl phosphonate and phosphonic acid compounds of formula (mm)

SCHEME VIII

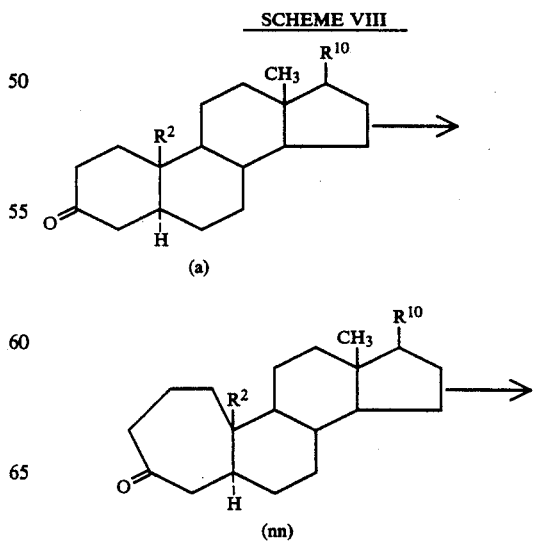

-continued
SCHEME VIII

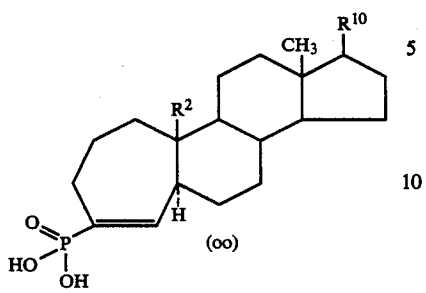

(oo)

Scheme VIII shows formation of Formula (I) compounds in which n is 2 from Scheme I, formula (a) compounds. Formula (nn) compounds are prepared by treatment of formula (a) compounds in a suitable organic solvent such as diethyl ether and methanol cooled to −20° C. to 20° C., preferably 0° C., with a strong base such as sodium hydroxide, lithium hydroxide, potassium carbonate, or, preferably potassium hydroxide (KOH), followed by treatment with a diazomethane precursor such as N-methyl N′-nitro-N-nitrosoquanidine, or, preferably N-methylnitrosourea. Substituting formula (nn) compounds for formula (a) compounds in the process of Scheme II yields formula (oo) compounds.

SCHEME IX

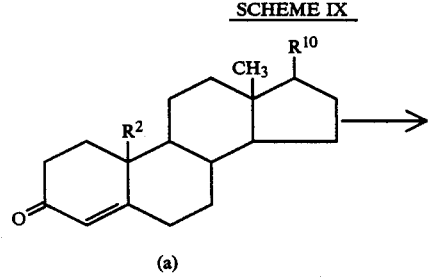

(a)

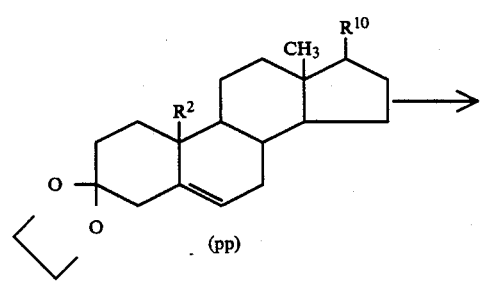

(pp)

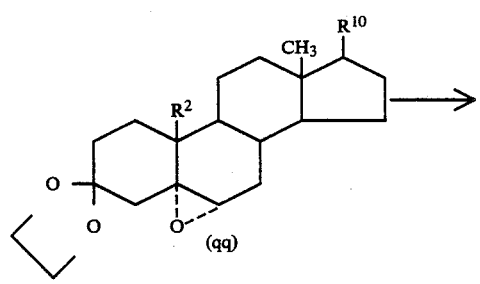

(qq)

-continued
SCHEME IX

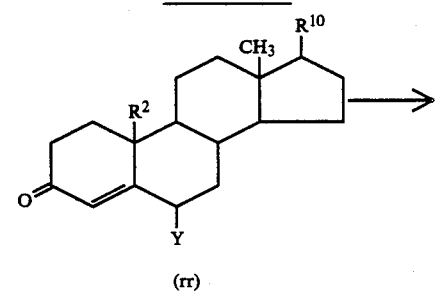

(rr)

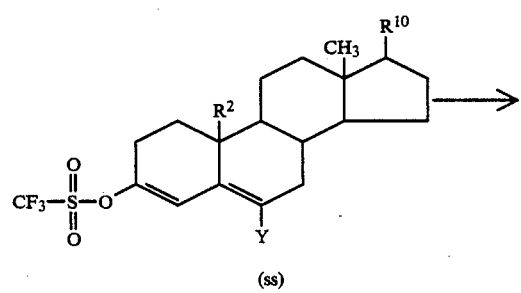

(ss)

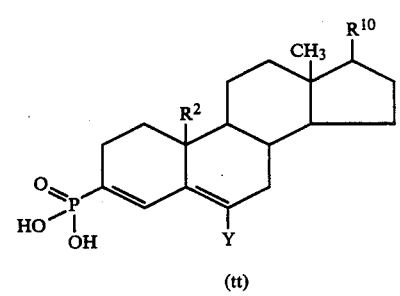

(tt)

Scheme IX outlines formation of Formula (Ia) compounds in which Y is chloro or fluoro from Scheme I, formula (a) compounds. Formula (pp) compounds are prepared by reacting formula (a) compounds with a suitable keto group protecting agent such as ethylene glycol in the presence of an acid catalyst such as p-toluenesulfonic acid. Treatment of formula (pp) compounds with a suitable oxidizing agent, preferably m chloroperbenzoic acid in a suitable organic solvent such as dichloromethane yields formula (qq) epoxide compounds.

Formula (rr) compounds then are prepared by adding gaseous hydrogen fluoride or hydrogen chloride to a formula (qq) compound in a suitable organic solvent such as chloroform, or (where Y is F) by adding borontrifluoride etherate to a formula (qq) compound in a suitable organic solvent, preferably benzene:ether followed by treatment with strong acid, preferably hydrogen chloride in glacial acetic acid. Next, 2,6-di-t-butyl-4-methvlpyridine followed by trifluoromethanesulfonic anhydride are added to a formula (rr) compound to yield a formula (ss) compound. Reaction of a formula (ss) compound by the procedures of Scheme I (b→c→d) gives formula (tt) phosphonic acid compounds of this invention. Compounds of Formula (I) in which Y is trifluoromethyl are prepared by processes such as exemplified in Example 26.

Compounds having a double bond at $C_{11}-C_{12}$ are prepared by modifications of the Schemes I through IX by procedures which would be apparent to those skilled in the art and are exemplified in Example 34, below.

The 3,5,11-triene compounds of Formula I are prepared from 11 oxo compounds by reaction in an appropriate solvent such as methylene chloride with a base such as 2,6-di-t-butyl-4-methylpyridine and a trihaloakyl sulfonic anhydride such as trifluoromethane sulfonic anhydride to give an 11 trifluorosulfonate (triflate) compound. The triflate group is eliminated to provide the 3,5,11-triene compounds.

The 2-ene compounds of Formula I are prepared by converting 52 3-oxo compounds to 52-2-ene-3-triflates in an appropriate solvent such as tetrahydrofluran with lithium bis(trimethylsilyl) amide and a sulfonating agent such as N-phenyltrifluoromethanesulfonimide at a reduced temperature of about −100° to 20° C. The triflate compounds are converted to 3-dimethyl phosphonate compounds by procedures of Scheme I and II followed by hydrolysis of the phosphonate ester groups with, for example, trimethylsilyl iodide to provide 3-phosphonic acid compounds Catalytic hydroqenation of the 2-ene compounds of Formula I provide the A-ring saturated compounds of Formula I.

Another aspect of this invention relates to the palladium catalyzed coupling of a 3-trifluoromethylsulfonate steroid, such as formula (b) of Scheme I with a phosphite such as a dialkylphosphite preferably dimethylphosphite to give a dimethyl steroidal-3-phosphonate, such as formula (c) of Scheme I.

In the above Schemes, the starting materials are selected so that the $R^2$ and $R^{10}$ groups in the formula (a) compound are the same as the $R^2$ and R groups in the Formula (I) compound being synthesized. Alternatively, the $R^2$ and $R^{10}$ group of the formula (a) compound are selected so that they can be converted by known procedures to the $R^2$ and R groups of the target Formula (I) compound by additional steps in the synthetic process. For example, Formula (I) compounds wherein R is carboxylic acid are converted to the corresponding esters by reaction with acid anhydrides or halides.

Pharmaceutically acceptable acid addition salts of the compounds of the invention containing a basic group are formed where appropriate with strong or moderately strong organic or inorganic acids by methods known to the art. For example, the basic compound of this invention is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the acid addition salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, choline, piperazine, and (trihydroxym-ethyl)methylamine.

Because Formula (I) compounds inhibit steroid 5α-reductase activity, they have therapeutic utility in treating diseases and conditions wherein decreases in DHT activity produce the desired therapeutic effect. Such diseases and conditions include acne vulqaris, seborrhea, female hirsutism, prostate diseases such as benign prostatic hypertrophy, and male pattern baldness. The potency of several compounds of the invention was tested for potency in inhibiting human steroid 5α-reductase using tissue from hyperplastic human prostates. In determining potency in inhibiting the human enzyme, the following procedure was employed:

Frozen human prostates were thawed and minced into small pieces ($5mm^3$) The tissue was homogenized in 3 to 5 volumes of 20 mM potassium phosphate, pH 6.5, buffer containing 0.33 M sucrose, 1 mM dithiothreitol, and 50 μM NADPH with a Brinkmann Polytron (Sybron Corporation Westbury, N.Y.). The solution was subjected to sonication for 3 to 5 minutes with a Sonifier (Branson Sonic Power Co.) followed by hand homogenization in a glass-to glass Dounce homogenizer (Kontes Glass Company, Vineland, N.J.).

Prostatic particles were obtained by differential centrifugation at 600 or 1000 x g for 20 minutes and 40,000 x q for 60 minutes at 4° C. The pellet obtained from the 140,000 x g centrifugation was washed with 5 to 0 tissue volumes of the buffer described above and recentrifuged at 140,000 x g. The resulting pellet was suspended in 20 mM potassium phosphate buffer, pH 6.5, containing 20% glycerol, 1 mM dithiothreitol, and 50 μM NADPH. The suspended particulate solution was stored at −80° C.

A constant amount of [$^{14}$C]-testosterone (52 to 55 mCi/mmol, New England Nuclear, Boston, Mass.) in ethanol and varying amounts of the potential inhibitor in ethanol were deposited in test tubes and concentrated to dryness in a SAVANT Speed Vac. To each tube was added buffer, 20 μl of 10 mM NADPH and an aliquot of prostatic particulate solution to a final volume of 1.0 ml of 50 mM sodium citrate, pH 5.0. After incubating the solution at 37° C. for 20 to 30 minutes the reaction was quenched by the addition of 4 ml ethyl acetate and 0.25 μmol each of testosterone, dihydrotestosterone, androstanediol, and androstanedione as carriers. The organic layer was removed to a second test tube and evaporated to dryness in a Speed Vac. The residue was dissolved in 20 to 30 μl chloroform, spotted on an individual lane of a 20×20 cm prechannelled silica gel TLC plate (Si 250F PA, Baker Chemical) and developed twice with acetone:chloroform (1:9). The radiochemical content in the bands of the substrate and the products was determined with a BIOSCAN Imaging Scanner (Bioscan, Inc., Washington, D.C.). The percent of recovered radiolabel converted to product was calculated, from which enzyme activity was determined. All incubations were conducted such that no more than 12% of the substrate (testosterone) was consumed.

The experimentally obtained data was computer fitted to a linear function by plotting the reciprocal of the enzyme activity (1/velocity) against the variable inhibitor concentration (Dixon, M. (1953), *Biochem. J.*, 55, 170). Assuming that the steroidal inhibitor is a competitive inhibitor against testosterone, a value for the inhibition constant ($K_i$) can be calculated from equation 1:

$$K_i = (B/A)/(S/K_m + 1) \qquad \text{Equation 1}$$

where B is the intercept on the 1/velocity axis, A is the slope of the line, S is the concentration of substrate (testosterone) used in the experiment, and $K_m$ is the Michaelis-Menton constant of the substrate (testosterone) determined in a separate experiment to be 4.5 μM.

Table II displays the results of the above testing and shows that the tested compounds of the invention are potent inhibitors of human steroid 5α-reductase.

TABLE II

Inhibition Constants of Human Prostatic Steroid 5α-Reductase

| Compound | $K_i$(nM) |
|---|---|
| Example 1 | 15–40 |
| Example 30 | 160 |

In vivo activity in inhibiting steroid 5α-reductase activity may be demonstrated by the following procedure. Male Charles River CD rats, 48 days old, weighing approximately 200 gm are administered the compound to be tested dissolved in propylene glycol and diluted in normal saline. Following compound administration the animals are sacrificed, the ventral prostates are excised, and DHT levels are measured by the following procedure.

Prostate tissue is excised, trimmed, weighed, minced and washed with phosphate buffer. The tissue then is homogenized in phosphate buffer and extracted by addition of ethyl acetate and mixing on an orbital mixer for forty-five minutes. The ethyl acetate is evaporated, the residue is reconstituted in ethanol, and is centrifuqe filtered using 0.45 μM filter paper. The components then are separated using reverse-phase HPLC collecting the DHT fraction. The fraction is reduced to dryness and reconstituted in standard DHT assay buffer available from Amersham. DHT levels then are measured using standard techniques such as radioimmunoassay.

The compounds of Formula (I) are incorporated into convenient pharmaceutical dosaqe forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds of Formula (I) in a pharmaceutical dosage unit as described above will be an efficacious, nontoxic quantity selected from the range of 0.001–100 mg/kg of active compound, preferably 0.01–10 mg/kg. The selected dose is administered to a human patient in need of steroid 5α-reductase inhibition from 1–6 times daily, topically, orally, rectally, by injection, or continuously by infusion or less often than once a day depending on the pharmacokinetics of the compound. Oral dosage units for human administration preferably contain from 1 to 500 mg of active compound. Parenteral administration uses lower dosages.

Oral administration is preferred and convenient for the patient.

The method of this invention of inhibiting steroid 5α-reductase activity in mammals, including humans, comprises administering internally to a subject in need of such inhibition an effective steroid 5α-reductase inhibiting amount of a compound of Formula (I).

Contemplated equivalents of Formula I compounds are compounds otherwise corresponding thereto wherein substituents have been added to any of the unsubstituted positions of the Formula (I) compounds or the methyl group at C-13 is absent or replaced by $C_{1-4}$alkyl provided such compounds have the pharmaceutical utility of Formula (I) compounds.

The following examples illustrate preparation of compounds and pharmaceutical compositions of this invention. The examples are not intended to limit the scope of the invention as defined hereinabove and as claimed below.

EXAMPLE 1

17β-(N,N-Diisooropvlcarboxamide)androst-3.5-diene-3-ohosophonic acid (i) Androst-4-ene-3-one-17β-carboxvlic acid Methyl androst-4-ene-3-one-17β-carboxylate (20 g, mmol) was dissolved in 700 ml of a 20:1 solution of methanol:water and potassium hydroxide (7 g) was added and the solution was refluxed under argon for 24 hours. The reaction mixture was then acidified with 5% hydrochloric acid and 250 ml water was added. After aging for 1 hour, the mixture was filtered and dried to yield 18 g (94%) of androst-4-ene-3-one-17β-carboxylic acid as a white crystalline solid.

(ii) Androst-4-ene-3-one-17β-N,N-diisooroovl-carboxamide

A solution of androst-4-ene-3-one-17β-carboxylic acid (18 g, 0.06 mol) in 350 ml of toluene was azeotropically dried until approximately 100 ml distillate was collected. The solution was then cooled to 10° C. Pyridine (6.7 ml, 0.08 mol) was added, followed by slow addition of a solution of oxalyl chloride (7.2 ml, 0.08 mol) in 10 ml of toluene. The reaction mixture was stirred at room temperature (under argon) for 2 hours, and then cooled to 0° C. A solution of diisopropylamine (89 ml, 0.6 mol) in 40 ml toluene was added dropwise such that the temperature did not exceed 40° C. The reaction mixture was stirred for 1 hour and then quenched with 300 ml ice water. The layers were separated and the aqueous layer was extracted 4 times with ethyl acetate (800 ml). The organic layers were combined and washed with 5% hydrochloric acid and brine. The organic layer was then dried over sodium sulfate and concentrated to dryness. Recrystallization by dissolving in 10 ml toluene and adding 200 ml hexane afforded 16.5 g (69%) of androst-4-ene-3-one-17β-N,N-diisopropylcarboxamide (m.p. 236°–239° C.).

(iii) 17β-(N.N-Diisopropylcarboxamide)-3-(trifluoromethvlsulfonate)-androst-3,5-diene Androst-4-ene-3-one-17β-N,N-diisopropylcarboxamide (5 g, 12.5 mmol) was dissolved into 50 ml of methylene chloride. 2,6-Di-t-butyl-4-methylpyridine (3.08 g, 17.0 mmol) was then added to the steroid solution and stirred at room temperature for 15 minutes. Trifluoromethane sulfonic anhydride (3.5 ml, 19 mmol) was added to the solution and stirring continued for 30 minutes. The reaction mixture was then diluted with 50 ml methylene chloride and filtered. The organic layer was washed twice with 5% hydrochloric acid, saturated sodium bicarbonate, and brine. It was then dried over sodium sulfate and evaporated. The triflate was purified by chromatography on silica gel eluting with 20% ethyl acetate in hexane to yield 4 g (61%) of 17β-(N,N-diisopropylcarboxamide)-3-(trifluoromethylsulfonate)-androst-3,5-diene.

(iv) Dimethyl 17β-(N,N-diisooroo Ylcarboxamide)-androst-3,5-diene-3-phosohonate

To a solution of 2.39 g (4.5 mmole) of 17β-(N,N-diisopropylcarboxamide)-3-trifluoromethylsulfonate-androst-3,5-diene in 50 mL of DMF was added 2.6 mL (4 equivalents) of triethylamine and 0.5 mL (1.1 eq.) of dimethyl phosphite. The solution was flushed with argon, 292 mg (0.05 eq.) of tetrakis (triphenylphosphine) palladium (o) were added, the mixture was stirred under argon for 1 hour and then poured into water. The product was extracted into methylene chloride and the organic layer was washed with water (3×), dilute HCl (1×), saturated NaHCO3 and brine. The dried, concentrated product was chromatographed on silica gel with an ethyl acetate/hexane gradient. The product (eluted with 1:1 ethyl acetate in hexane) on drying gave 1.48 g (67%) of dimethyl 17β-(N,N-diisopropyl-carboxamide)-androst-3,5-diene-3-phosphonate. NMR: 0.78 ppm (s,3); 0.93 ppm (s,3); 3.42 ppm (m,l); 3.68 ppm (s,3); 3.75 ppm (s,3); 4.24 ppm (m,l); 5.84 ppm (s,l); 6.80 ppm (d,l).

(v) 17β-(N,N-Diisopropylcarboxamide)-androst-3,5-diene-3-ohosohonic acid.

In 5 mL of acetonitrile was dissolved 250 mg (0.5 mmole) of dimethyl 17β-(N,N-diisopropylcarboxamide)-androst-3, 5-diene-3-phosphonate. The solution was flushed with argon and 150 mg (1 mmole) of sodium iodide and 0.13 mL (1 mmole) of trimethylsilyl chloride was added. The reaction mixture was stirred at room temperature under argon for 24 hours, diluted with chloroform and the organic layer was washed with water, dilute HCl, brine and sodium sulfite solution. The dried concentrated product (232 mg) was purified by HPLC on a reverse phase C-18 column eluting with 70% methanol and 30% of 20 mmole phosphate buffer (pH 6.6) to afford 17β-(N,N-diisopropylcarboxamide)-androst-3,5-diene-3phosphonic acid as a white crystalline solid; m.p. 240°-243° C.

EXAMPLE 2

20α-(Hydroxvmethyl)-5α-oreon-3-ene-3-phosphonic acid (i) 20α-(Hvdroxomethvl)-preon-4-ene-3-one Pregn-4-ene 3-one-20α-carboxaldehyde (16.4 g, 50 mmol) in ethanol (250 ml) and THF (50 ml) was cooled to 0° C. and a solution of sodium borohydride (NaBH4) in 125 ml ethanol was added dropwise. The reaction mixture was stirred overnight at 25° C. Acetic acid was added to the reaction mixture until neutral pH and then the solution was evaporated to remove excess ethanol. The residue was dissolved in trichloromethane and washed with saturated sodium bicarbonate solution, water and brine. The organic layer was then dried over sodium sulfate and evaporated to dryness to yield 13.9 g (82%) of 20α-(hydroxymethyl)-pregn-4-ene-3-one.

(ii) 20α-(t-Butvldimethvlsilvloxvmethvl)-pregn-4-ene-3-one

A solution of 20α-(hydroxymethyl)-pregn-4-ene-3-one (1.2 g, 3.5 mmol), t-butyldimethylsilyl chloride (627 mg, 4.15 mmol) and imidazole (287 mg, 4.22 mmol) in DMF (40 ml) was stirred overnight at 40° C. The reaction mixture was then poured into ice water and the emulsion was washed three times with ethyl acetate. The organic layers were combined, washed with cold dilute hydrochloric acid, water and brine; dried over sodium sulfate and evaporated to dryness. Recrystallization from methanol afforded 1.1 g (70%) of 20α-(t-butyldimethylsilyloxy-methyl)pregn-4-ene-3-one.

(iii) 20α-(t-Butvldimethvlsilvloxvmethvl)-3-trifluoromethvlsulfonate)-5α-oreon-3-ene Ammonia (200 ml) was double distilled into a 3-neck roundbottom flask equipped with a dry ice condenser and argon bubbler. Lithium (Li) wire (120 mg, 17.4 mmol) was dissolved in ammonia (NH3). A solution of 20α-(t-butyldimethylsilyloxymethyl)-pregn-4-ene-3-one (3 g, 6.76 mmol) and aniline (49.5 1, 5.4 mmol) in THF (50 ml) was added dropwise to the Li/NH3 solution. The reaction mixture was stirred at −78° C. for 15 minutes and then quenched with isoprene until the blue color disappeared. The volatiles were slowly evaporated (to avoid excess foaming) by slow warming, and eventually at 0.5 mmHg for 1 and ½ hours. The residue was redissolved in THF (50 ml) and cooled to 0° C. A solution of N-phenyltrifluoromethylsulfonimide (7 g, 20 mmol) in THF (10 ml) was added to the reaction mixture, and stirring was continued overnight at 4° C. The solvent was then evaporated and the residue was chromatographed on silica gel eluting with 3% ethyl acetate in hexane to yield 2.24 g (57%) of the 20α-(t-butyldimethylsiloxymethyl)-3-(trifluoromethylsulfonate)-5α-pregn-3-ene.

(iv) Dimethvl 20α-(t-hutvldimethvlsilvloxv-methvl)5α-oreon-3-ene-3-ohosohonate

20α-(t-Butyldimethylsilyloxymethyl)-3-(trifluoromethylsulfonate)-5α-pregn-3-ene (100 mg, 0.173 mmol) in DMF (1 ml) is treated with triethylamine, ethyl phosphite and tetrakis-triphenylphosphine) palladium (o) by the procedure of Example 1 to give the title compound (iv).

(v) Dimethvl 20α-(hydroxymethyl)-5-α-oreon-3-ene-3-phogphonale

Dimethyl 20α-(t-butyldimethylsilyloxymethyl)-5α-pregn-3-ene-3-phosphonate (500 mg) is dissolved in THF (20 ml) and 2 ml of a 1 molar solution of tetrabutylammonium fluoride in THF was added. The reaction mixture is stirred at room temperature for 3.5 hours and then diluted with water. The aqueous mixture is washed thoroughly with dichloromethane. The organic layers are combined, dried over sodium sulfate and evaporated to dryness. Purification by flash chromatography eluting ethyl acetate in hexane afforded dimethyl 20α-hydroxymethyl-5α-pregn-3-ene-3-phosphonate.

(vi)
20α-(Hydroxymethyl)-5α-oreon-3-ene-3-ohosohonic acid Dimethyl

20α-(hydroxymethyl)-5α-pregn-3-ene-3-phosphonate in acetonitrile is treated with NaI and TMS-Cl by the procedure of Example 1 to give the title compound (vi).

EXAMPLE 3
17β-(N,N-Diisooroovlcarboxamide-5α-androst-3-ene-3-ohosohonic acid

(i) 17β-(Hvdroxvmethvl)-androst-4-ene-3-ol

Approximately 750 ml of dry THF was added to a 3-neck round bottom flask equipped with a condenser, argon bubbler and mechanical stirrer. The flask was cooled to 0° C. and lithium aluminum hydride (LAH) (11.39 g, 0.3 mol) was slowly added. After all of the LAH was added, the flask was warmed to room temperature. A solution of methyl androst-4-ene-3-one-17βB-carboxylate (66 g, 0.2 mol) in 600 ml of THF was very slowly added to the LAH slurry. After the addition of the steroid, the reaction mixture was slowly warmed to reflux. After 2 hours the excess LAH was quenched with 11.4 ml water, 11.4 ml 15% sodium hydroxide (NaOH) and 28 ml water. The salts were removed by filtration and washed with approximately 1 liter of warm THF. Concentration of the combined organic solutions afforded 63 g (94%) of 17β-(hydroxymethyl)-androst-4-ene-3-ol as mixture of α and β isomers.

(ii) 3-Oxo-17β-(hvdroxvmethvl)-4-androstene

A solution of 17β-(hydroxymethyl)-androst-4-ene-3-ol (27 g, 0.089 mol) in 1200 ml trichloromethane was treated with activated manganese dioxide (66 g). After 3 hours the mixture was filtered. Concentration afforded 26 g (96%) of 3-oxo-17β-(hydroxymethyl)-4-androstene (m.p. 151° C.).

(iii) 3-Oxo-17β-(t-butvldimethvlsilvloxvmethvl)-4-androstene

To a solution of 3-oxo-17β-(hydroxymethyl)-4-androstene (15 g, 0.05 mol) in 200 ml DMF was added 5.8 g (0.085 mol) imidazole followed by 9.7 g (0.065 mol) t-butyldimethylsilyl chloride. The reaction mixture was stirred at room temperature under argon, for 2.5 hours. The reaction mixture was then poured into 250 ml ice water and washed 3 times with ethyl acetate. The combined organic layers were washed twice with cold 5% hydrochloric acid and once each with saturated sodium bicarbonate solution and brine. The organic layer was dried over sodium sulfate and evaporated. Recrystallization from methanol afforded 16.9 g (82%) of 3-oxo-17β-(t-butyldimethylsilyloxymethyl)-4-androstene as a white crystalline solid.

(iv) 17β-(t-Butyldimethylsilyloxymethyl)-3-(trifluoromethvlsulfonate)-5α-androst-3-ene Ammonia (300 ml) was double distilled into a 3-neck round bottom flask equipped with a dry ice condenser and argon bubbler Li wire, 250 mg (3 eq), was dissolved in the ammonia and stirred for 15 minutes to ensure dryness. Freshly distilled aniline, 0.53 ml (0.8 eq), was then added. A solution of 3 g (7.2 mmol) of 3-oxo-17β-(t-butyldimethylsilyloxymethyl)-4-androstene in 50 ml of dry THF was added dropwise to the Li/NH solution. An additional 50 ml dry THF was added to aid in solubility. The reaction mixture was stirred at −78° C. for 2 hours and then quenched with isoprene until the blue color disappeared. The volatiles were slowly evaporated (to avoid excess foaming) by slow warming, and eventually at 0.5 mmHg for 1.5 hours. The oily residue was redissolved in dry THF (100 ml) and cooled to 0° C. A solution of 7.7 g (3 eq) of N-phenyltrifluoromethylsulfonimide in 50 ml THF was added, the flask was tightly sealed, and stirred overnight at 4° C. The mixture was then concentrated to dryness, and chromatographed on silica eluting with hexane. Recrystallization from ethyl acetate yielded 2.5 g (63%) of 17β-(t-butyldimethylsilyloxymethyl)-3-(trifluoromethylsulfonate)-5α-androst-3-ene (m.p. 120°-121° C.).

(v) Dimethyl 178β-(t-butyldimethylsilyloxymethyl)-5α-androst-3-ene-3-ohosohonate c To a solution of 3 g (5.46 mmol) of 17β-(t-butyldimethylsilyloxymethyl)-3-(trifluoromethylsulfonate)-5α-androst-3-ene in 10 ml DMF is treated within triethylamine and tetrakis (triphenylphosphine)palladium (0) by the procedure of Example 1 to give the title compound (v).

(vi) 3-Dimethylphosphono-3-androstene-17β-carboxylic acid

Dimethyl 17β-(t-butyldimethylsilyloxymethyl)-5α-androst-3-ene-3-phosphonate (500 mg), was dissolved in 150 ml acetone. Jones reagent was added until a red color persisted. Isopropanol was then added to quench excess Jones reagent. The acetone was decanted off and the residual chromium salts were then dissolved in water and washed 3 times with dichloromethane. The organic layers were combined and passed through a plug of florosil and concentrated to give 360 mg (99%) of 3-dimethylphosphono-3-androstene-17β-carboxylic acid.

(vii) Dimethyl 17β-N,N-diisopropylcarboxamide-3-androstene-3-phosohonate

3-Dimethylphosphono-3-androstene-17β-carboxylic acid, (360 mg, 0.78 mmol) was suspended in 10 ml of dry toluene and treated with 0.4 ml of oxalyl chloride for 2 hours under argon. The reaction mixture was then evaporated (1 mm Hg) and the residue was dissolved in 10 ml dry THF. A solution of 0.6 ml diisopropylamine in 2 ml dry THF was added and the reaction mixture stirred for 1 hour. The mixture was diluted with ice water and extracted with dichloromethane. The organic layer was then washed twice with cold 5% hydrochloric acid, sodium hydroxide and brine; dried over sodium sulfate and evaporated. Chromatography on silica gel eluting with 20% ethyl acetate in hexane followed by recrystallization from diethyl ether afforded the title compound.

(viii) 17β-(N,N-diisopropylcarboxamine)-5α-androst-3-ene-3-phosphonic acid.

Dimethyl 17β-(N,N-diisopropylcarboxamide)-3-androstene-3-phosphonate in acetonitrile is treated with NaI and TMS-Cl by the procedure of Example 1 to give the title compound.

EXAMPLE 3A

(i) Dimethyl 17β-(N,N-diisopropylcarboxamide)-5α-adrost-3-ene-3-phosphonate

A solution of 17β-(N,N-diisopropylcarboxamide)-3-trifluori-methylsulfonate-5α-androst-3-ene (200 mg), prepared using 17β-(N,N-diisopropylcarboxamide)-3-oxo-5α-androst-3-ene in the procedure of Example 3(iv), in 40 mL of DMF and 0.2 mL of triethylamine was stirred with tetrakis (triphenylphosphine) palladium (0) (35 mg) and 0.5 mL of dimethyl phosphite under argon at ambient temperature and worked up as described in Example 1 (iv) to give 150 mg (82%) yield of dimethyl 17β-N,N-diisopropylcarboxamido-5α-androst-3-ene-3-phosphonate.

(ii) 17β-(N,N-diisopropylcarboxamide)-5α-androst-3-ene-3-phosphonic acid.

The preparation of the title compound is analogous to Example 1 (v) by using dimethyl 17β-(N,N-diisopropylcarboxamide)-androst-3,3-diene-3-phosphonate.

EXAMPLE 4

17β-(N,N-Diisopropylcarboxamide)-4-fluro-5α-androst-3-ene-3-phosphonic Acid

(i) 3-Oxo-17β-(hydroxymethyl)-5-α-androstane

Ammonia (500 ml) was distilled into a 3-neck round-bottom flask equipped with a dry ice condenser and argon bubbler. Li wire (3 g) was dissolved in the ammonia and stirred for 15 minutes to ensure dryness. A solution of 3-oxo-17β-(hydroxymethyl)-4-androstene (prepared as described in Example 2 (ii), 37.5 g, 0.123 mol) in 625 ml THF and t-butyl alcohol (6.25 ml, 0.8 eq) was added dropwise to the Li/NH$_3$ solution. The reaction was stirred at −78° C. for 2 hours and quenched with isoprene until the blue color disappeared. The resulting enolate was then quenched with ammonium chloride and the ammonia was allowed to evaporate. Acetone was added to the residue and gently refluxed. The acetone solution was then filtered and evaporated to dryness to yield 24.7 g (79%) of 3-oxo-17β-(hydroxymethyl)-5-androstane.

(ii) 3-Oxo-5α-androstane-17β-carboxylic acid

The title compound was prepared according to Example 3 (ii) by replacing 3-oxo-17β-(hydroxymethyl)-5α-androstane for dimethyl 17β-(t-butyldimethylsilyloxymethyl)-5α-androst-3-ene-3-phosphonate.

(iii) 3-Oxo-5α-androstane-17β-N,N-diisopropylcarboxamide

3-Oxo-5α-androstane-17β-carboxylic acid was suspended in toluene (100 ml) and an excess of oxalyl chloride (8 ml) was added. The reaction mixture was stirred for 1 hour at 25° C. (under argon). The volatiles were then removed (0.5 mmHg for 2 hours). The residue was resuspended in THF (25 ml), cooled to 0° C., and diisopropyl amine (10 ml) was added. The reaction mixture was stirred at 0° C. for 2 hours and then diluted with water. The aqueous mixture was extracted with ethyl acetate and evaporated. Purification by chromatography on silica gel eluting with 20% ethyl acetate in hexane afforded 3.15 g (78%) of 3-oxo-5α-androstane-17β-N,N-diisopropylcarboxamide.

(iv) 3-Oxo-5α-androst-1-ene-17β-N,N-diisopropylcarboxamide

To a solution of 3-oxo-5α-androstane-17β-N,N-diisopropylcarboxamide (2.3 g, 5.74 mmol) in 100 ml ethyl acetate was added phenylselenylchloride (1.1 g, 5.74 mmol) and the reaction mixture was stirred for 2 hours. The reaction mixture was then washed with 5% sodium bicarbonate solution and brine. The ethyl acetate solution was cooled to 0° C. and 50 ml THF was added. Hydrogen peroxide (6 ml of a 30% solution) was slowly added and the reaction mixture stirred for 2 hours. The reaction mixture was then washed with 5% sodium bicarbonate solution, brine and evaporated to dryness. Purification by chromatography on silica gel eluting with 20% ethyl acetate in hexane afforded 1.3 g (56.5%) of 3-oxo-5α-androst-1-ene-17β-N,N-diisopropylcarboxamide.

(v) 3-Oxo-5α-androstane-1,2-alpha-epoxide-17β-N,N-diisopropylcarboxamide

3-Oxo-5α-androst-1-ene-17β-N,N-diisopropylcarboxamide (4.6 g, 11.5 mmol) was dissolved in 50 ml methanol and cooled to 15° C. To the solution was added hydrogen peroxide (0.8 ml of a 30% solution) followed by sodium hydroxide (0.16 ml of a 10% solution) in 2 ml methanol. The ice bath was removed and stirring was continued at room temperature for 1 hour. The reaction mixture was then poured into ice water and washed twice with dichloromethane. The organic layers were combined and washed with water and brine; dried over sodium sulfate and evaporated. Trituration in acetone afforded 4.0 g (83.7%) of the desired epoxide; 3-oxo-5α-androstane-1,2α-epoxide-17β-N,N-diisopropylcarboxamide.

(vi) 3-Oxo-4-fluoro-5α-androst-1-ene-17β-N,N-diisopropylcarboxamide

3-Oxo-5α-androstane-1,2α-epoxide-17β-N,N-diisopropylcarboxamide (1.7 g, 4 mmol) was dissolved in 25 ml THF and cooled to −20° C. Pyridinium poly(hydrogen fluoride) (10 ml) was slowly added to the solution (under argon). The reaction mixture was warmed to 0° C., stirred 30 minutes then warmed to room temperature and stirred for 15 minutes. The reaction mixture was poured into ice water and washed with ethyl acetate. The organic layer was washed with water, 5% sodium bicarbonate solution and brine; dried over sodium sulfate and evaporated. Purification by chromatography on silica gel eluting with 20% ethyl acetate in hexane yielded 750 mg (44%) of the desired 3-oxo-4-fluoro-5α-androst-1-ene-17β-N,N-diisopropylcarboxamide.

(vii) 17β-(N,N-Diisopropylcarboxamide)-3-(trifluoromethylsulfonate)-4-fluoro-5α-androst-1,3-diene A solution of lithium bis(trimethylsilyl)amide (4.2 mmol, 2.2 eq) in 2 ml THF was cooled to −78° C. A solution of 3-oxo-4-fluoro-5α-androst-1-ene-17β-N,N-diisopropylcarboxamide (800 mg, 1.9 mmol) in 10 ml THF was added and the reaction mixture was stirred for 1 hour. A solution of N-phenyltrifluoromethanesulfonimide (857 mg, 2.4 mmol) in 8 ml THF was then added and the reaction mixture was stirred for 1.5 hours at −78° C. The reaction mixture was then evaporated to dryness and chromatographed on silica gel eluting with 20% ethyl acetate in hexane. Trituration in a hexane and ether solution afforded 460 mg (46%) of the desired product, 17β-(N,N-diisopropylcarboxamide)-3-(trifluoromethylsulfonate)-4-fluoro-5α-androst-1,3-diene.

(viii) Dimethyl 17β-(N,N-diisopropylcarboxamide)-4-fluro-5α-androst-1,3,-diene-3-phosphonate The title compound is prepared according to Example 1 (iv) by using 17β-(N,N-diisopropylcarboxamide)-3-trifluoromethylsulfonate-4-fluoro-5β-androst-1,3 diene in place of 17β-N,N-diisopropyl-carboxamide-3-trifluoromethylsulfonate-androst-3,5-diene.

(ix) Dimethyl 17β-(N,N-diisopropylcarboxamide)-4-fluro-5α-androst-3-ene-3-phosphonate Dimethyl 17β-(N,N-diisopropylcarboxamide)-4-fluoro-5α-androst-1,3-diene phosphonate (150 mg) in 20 mL of a 3:1 solution of ethyl acetate and hexane was hydrogenated at 25° C. and 1 atmosphere over 30 mg of 10% of palladium on carbon. The suspension was filtered and concentrated to a white solid (150 mg). Trituration with methanol/acetone provided 70 mg of dimethyl 17β-(N,N-diisopropylcarboxamide)-4-fluoro-5α-androst-3-ene-3phosphonate. The title compound had a m.p. 165°–168° C.

(x) 17β-(N,N-diisopropylcarboxamide)-4-fluoro-5α-androst-3-ene-3-phosphonic acid The title compound is prepared according to Example 1 (v) by using dimethyl 17β-N,N-diisopropylcarboxamide-4-fluoro-5α-androst-3-ene-phosphonate in place of dimethyl 17β-(N,N-diisopropylcarboxamide)androst-3,5-diene-3-phosphonate; m.p. 222°–225° C.

EXAMPLE 5

20α-(Hydroxymethyl)-4-fluoro-5α-pregn-3-ene-3-carboxylic acid (i) 20α-(Hydroxymethyl)-5α-pregnan-3-one The title compound was prepared according to Example 4 (i) by substituting 20α-(hydroxymethyl)-pregn-4-ene-3-one for 3-oxo-17β-(hydroxymethyl)-4-androstene.

(ii) 20α-(Hydroxymethyl)-5α-pregn-1-ene-3-one

The title compound was prepared according to Example 4 (iv) by substituting 20α-(hydroxymethyl)-5α-pregnane-3-one for 3-oxo-5α-androstane-17β-N,N-diisopropylcarboxamide.

(iii) 20α-(Hydroxymethyl)-1,2α-epoxide-5α-pregnan-3-one

The title compound was prepared according to Example 4 (v) by substituting 20α-(hydroxymethyl)-5α-pregn-1-ene-3-one for 3-oxo-5α-androst-1-ene-17β-N,N-diisopropylcarboxamide.

(iv) 20α-(Hydroxymethyl)-4-fluoro-5α-pregn-1-ene-3-one

The title compound was prepared according to Example 4 (vi) by substituting 20α-(hydroxymethyl)-1,2α-epoxide-5α-pregnane-3-one for 3-oxo-1,2α-androstane-17β-N,N-diisopropylcarboxamide.

(v) 20α-(t-Butyldimethylsilyloxymethyl)-4-fluoro-5α-pregnan-1-ene-3-one

The title compound was prepared according to Example 2 (ii) by substituting 20α-(hydroxymethyl)-4-fluoro-5α-pregn-1-ene-3-one for 20α-(hydroxymethyl)-pregn-4-ene-3-one.

(vi) 20α-(t-Butyldimethylsilyloxymethyl)-4-fluoro-3-(trifluoromethylsulfonate) 5α-pregn-1,3-diene The title compound was prepared according to Example 4 (vii) by substituting 20α-(t-butyldimethylsilyloxymethyl)-4-fluoro-5α-pregn-1-ene-3-one for 3-oxo-4-fluoro-5α-androst-1-ene-17β-N,N-diisopropylcarboxamide.

(vii) Dimethyl 20-α-(t-butyldimethylsilyloxymethyl)-4-fluoro-5-α-pregn-1,3-diene-3-phosphonate The title compound was prepared according to Example 4 (viii) by substituting 20α-(t-butyldimethylsilyoxymethyl)-4-fluoro-3-(trifluoromethylsulfonate)-5α-pregn-1,3-diene for 17β-(N,N-diisopropylcarboxamide)-3-(trifluoromethylsulfonate)-4-fluoro-5α-androst-1,3-diene.

(viii) Dimethyl 20α-(t-butyldimethylsilyloxymethyl)-4-fluoro-5α-pregn-3-ene-3-phosphonate The title compound is prepared according to Example 4 (ix) by substituting dimethyl 20α-(t-butyldimethylsilyloxymethyl)-4-fluoro-5α-pregn-1,3-diene-3-phosphonate for dimethyl 17β-(N,N-diisopropylcarboxamide)-4-fluoro-5α-androst-1,3-diene-3-phosphonate.

(ix) Dimethyl 20α-(hydroxymethyl)-4-fluoro-5-pregn-3-ene-3-phosphonate

To a solution of dimethyl 20α-(t-butyldimethylsilyloxymethyl)-4-fluoro-5α-pregn-3-ene-3-phosphonate in THF is added tetrabutylammonium fluoride and the reaction mixture is stirred at 25° C. for 3.5 hours under argon. The reaction mixture was then poured into ether and washed with water and brine; dried over sodium sulfate and evaporated. Chromatography on silica gel eluting with 15% ethyl acetate in hexane yielded the desired dimethyl 20α-(hydroxymethyl)-4-fluoro-5α-pregn-3-ene-3phosphonate.

(x) 20α-(Hydroxymethyl)-4-fluoro-5α-pregn-3-ene-3-phosphonic acid

The title compound (is prepared according to Example 1 (v) by substituting 3-dimethyl 20α-(hydroxymethyl)-4-fluoro-5α-pregn-3-ene-3-phosphonate for dimethyl 17β-(N,N-diisopropylcarboxamide)-androst-3,5-diene-3-phosphonate.

EXAMPLE 6

17β-(N,N-Diisopropylcarboxamide)-A-nor-5α-androst-2-2-ene-2-phosphonic acid

(i)
17β-(N,N-Diisopropylcarboxamide)-3-oxo-5α-androstane

A mixture of 17β-(N,N-diisopropylcarboxamide)-3-oxo-androst-4-ene (2 g) in 150 mL of a 10:1 solution of ethyl acetate and acetic acid was hydrogenated at 25° and 1 atmosphere over 300 mg of 10% pd on charcoal. The suspension was filtered and the filtide concentrated to give 1.9 g of 17β-(N,N-diisopropylcarboxamide)-3-oxo-5α-androstane.

(ii)
17β-(N,N-Diisopropylcarboxamide)-A-nor-5α-androstane-2-carboxylic acid.

A solution of 17β-(N,N-diisopropylcarboxamide)-3oxo-5α-androstane (1 g) in 95% acetic sesquihydrate (3.85 g), and the mixture was heated in an oil both held at 80° C. for 2 hours under argon according to the procedure in Tetrachdron, 28, 5337–5339 (1972). The mixture was cooled, diluted with ice water and extracted with ethyl acetate. The organic extracts were washed to neutrality, dried and concentrated tot he crude product. A precipitation from methanol-acetone-ethyl ether gave 0.45 g of 17β-(N,N-diisopropylcarboxamide)-A-nor-5α-androstane-2-carboxylic acid.

(iii)
17β-(N,N-Diisopropylcarboxamide)-A-nor-3-oxo-5α-androstane

A solution of 17β-(N,N-diisopropylcarboxamide)-A-nor-5α-androstane-2-carboxylic ancie (432 mg, 1 mm) in 15 mL of dry THF and 2 mL of HMPA was added at −20° C. to lithium diisoproylamide (2.2. mmole) in 10 mL of THF. The mixture was stirred at −20° C. for 1 hour and at 0° C. after 30 minutes the reaction was guenched with ice water and extracted with ethyl acetate. The organic layer was washed with 2 N aqueous sodium bicarbonate solution, and these water washings were combined with the original water layer, cooled and acidified with HCl. The product was extracted into ethyl acetate, dried and concentrated to the sulfenylated acid. This crude product was dissolved in absolute ethanol (5 mL) anhydrous sodium bicarbonate (1.5 mmole) was added. Then solid N-chlorosuccinimide (2.3 mmole) was added portion . . . and the reaction mixture was stirred for 2 hours at 25°. A few drops of saturated aqueous sodium sulfite were added and this was followed by 2 mL of 1N HCl. After being stirred for 30 minutes, the reaction was diluted with water, extracted with ethyl acetate and washed with dilute NaHCO₃ solution. The dried, concentrated product afforded 17β-(N,N-diisopropylcarboxamide)-A-nor-2-oxo-5α-androstane after precipitation from acetone/hexane/ethyl ether.

(iv)
17β-N,N-Diisopropylcarboxamide)-A-nor-5α-androst-2-ene-2-phosphonic acid 17β-N,N-diisopropylcarboxamide-A-nor-2-oxo-2α-androstane was converted to the enol triflate by the method described in Example 4 using lithium bis (trimethylsilyl) amide and phenyltrifluoromethylsulfonimide. This triflate was reacted with dimethylphosphite according to Example 1 (iv) to provide dimethyl 17β-N,N-diisopropylcarboxamide-A-nor-5α-androst-2-ene-2-phosphonate, and this product, according to the procedure of Example 1 (v) provide 17β-(N,N-diisopropylcarboxamide)-A-nor-5α-androst-2-ene-2-phosphonic acid.

EXAMPLE 7

17β-(N,N-Diisopropylcarboxamide)-5α-androst-1.3-diene-3-phosphonic acid

(i)
17β-(N,N-Diisopropylcarboxamide)-3-(trifluoromethylsulfonate)-5α-androst-1,3-diene The title compound was prepared according to Example 4 (vii) by substituting 3-oxo-5α-androst-1-ene-17β-N,N-diisopropylcarboxamide for 3-oxo-4-fluoro-5 α-androst-1-ene-17β-N,N-diisopropylcarboxamide.

(ii) Dimethyl 17β-(N,N-diisopropylcarboxamide)-5α-androst-1,3-diene-3-phosohonate The title compound is prepared according to Example 1 (iv) by using 17β-(N,N-diisopropylcarboxamide)-3-(trifluoromethylsulfonate)-5α-androst-1,3-diene for as the starting material.

(iii)
17β-(N,N-Diisopropylcarboxamide)-5α-androst-1,3-diene-3-phosphonic acid The title compound is prepared according to Example 1 (v) by substituting dimethyl 17β-(N,N-diisopropylcarboxamide)-5α-androst-1,3-diene-3-phosphonate for dimethyl 17β-(N,N-diisopropylcarboxamide)-androst-3,5-diene-3-phosphonate.

EXAMPLE 8

19-Nor-5α-androst-3-ene-17β-ol-3-phosphonic acid

The title compound is prepared according to Example 1 (ii through vi) by substituting 19-nor-testosterone for 20α-(hydroxymethyl)-pregn-4-ene-3-one.

EXAMPLE 9

5α-Pregn-3-ene-(20R)-3,20-carboxy-3-phosphonic acid

(i) 3-Dimethylphosphono-5α-pregn-3-ene-(20R)-20-

To a solution of dimethyl 20α-(hydroxymethyl)-5α-pregn-3-ene-3-phosphonate, prepared as in Example 2, in acetone is added Jones reagent dropwise until a red color persists. Isopropanol is then added to quench the excess oxidant. The solution is decanted from the gummy chromium salts, concentrated, and partitioned between dichloromethane and water. The salts are dissolved in water and extracted with dichloromethane. The combined organic layers are then washed with brine, dried over sodium sulfate, and concentrated to yield 3-dimethyl-phosphono-5α-pregn-3-ene-(20R)-20-carboxylic acid.

(ii) 5α-Pregn-3-ene-(20R)-20-carboxy-3-phosohonic acid

The title compound is prepared according to Example 1 (v) by substituting 3-dimethylphosphono-5α-pregn-3-ene-(20R)-20-carboxylic acid for dimethyl-17β-(N,N-diisopropylcarboxamide)-androst-3,5-diene-3-phosphonate.

EXAMPLE 10

(20R)-20-(N,N-Diisopropylcarboxamide)-5α-pregn-3-ene-3-phosphonic acid

The title compound was prepared according to Example 3 (vii–viii) by substituting 3-dimethylphosphono-5-pregn-3-ene-(20R)-20-carboxylic acid, prepared as in Example 9, for 3-dimethylphosphono-3-androstene-17β-carboxylic acid.

EXAMPLE 11

5α-androst-3-ene-17β-carboxyaldehyde-3-phosphonic acid

(i)

3-Dimethylphosphono-5α-androst-3-ene-17β-carboxychloride

A solution of 3- dimethylphosphono-3-androstene-17β-carboxylic acid, prepared as in Example 3, is suspended in 10 ml toluene and treated with 0.5 ml of oxalyl chloride for 2 hours. The volatile materials are then removed at 1 mmHg leaving a residue of 3-dimethylphosphono-5α-androst-3-ene-17β-carboxylchloride.

(ii)

3-Dimethylphosphono-5α-androst-3-ene-17β-carboxyaldehyde

A solution of 3-dimethylphosphono-5α-androst-3-ene-17β-carboxylchloride in 10 ml tetrahydrofuran is treated with lithium tri-t-butoxyaluminum hydride at 0° C. for one hour to yield, after aqueous workup, 3-dimethylphosphono-5α-androst-3-ene-17β-carboxyaldehyde.

(iii)

5α-3-Androst-3-ene-17β-carboxyaldehyde-3-phosphonic acid

The title compound is prepared according to Example 3 (viii) by substituting 3-methylphosphono-5α-androst-3-ene-17β-carboxyaldehyde for dimethyl androstene-3-phosphonate-17β-N,N-diisopropylcarboxamide)-3-androstene-3-phosphonate.

EXAMPLE 12

5α-Androst-3-ene-17β-(1-oxobutyl)-3-phosphonic acid

(i)

3-Dimethylphosphono-17β-(1-oxobutyl)-5α-androst-3-ene

A solution of 3-dimethylphosphono-5α-androst-3-ene-17β-carboxylchloride (1 mmol), prepared as in Example 11, in THF is treated with 1.0 mmol of di-n-butylcopper lithium at −78° C. The reaction is quenched with aqueous ammonium chloride. Extraction with dichloromethane followed by concentration of the organic extracts and chromatography of the residue yields 3-dimethylphosphono-17β-(1-oxobutyl)-5α-androst-3-ene.

(ii) 5α-Androst-3-ene-17β-(1-oxobutyl)-3-phosphonic acid

The title compound is prepared according to Example 1 (v) by substituting 3-dimethyl-phosphono-17β-(1-oxobutyl)-5α-androst-3-ene for dimethyl 17β-(N,N-diisopropylcarboxamide)-androst-3,5-diene-3-phosphonate.

EXAMPLE 13

Androst-3,5-diene-17β-ol-3-phosphonic acid

The title compound is prepared according to Example 1 (iii through v) by substituting commercially available testosterone acetate for androst-4-ene-3-one-17β-N,N-diisopropylcarboxamide.

EXAMPLE 14

Androst-3,5-diene-17-one-3-phosphonic acid

The title compound is prepared according to Example 9 (i) by substituting androst-3,5-diene-17β-ol-3-phosphonic acid (Example 13) for dimethyl 20α-(hydroxymethyl)-5α-pregn-3-ene-3-phosphonate.

EXAMPLE 15

Ethyl pregn-3,5,17(20)-triene-3-phosphono-21-oate

A solution of sodium ethoxide (680 mg, 10 mmol) in 5 ml ethanol is added to a mixture of androst-3,5-diene-17-one-3-phosphonic acid (942 mg, 3 mmol) prepared as in Example 14, and methyl diethylphosphonoacetate (2.12 g, 10 mmol) and the resulting mixture heated at reflux for 4 hours. The mixture is cooled, concentrated, diluted with dilute acetic acid and washed with ether. The combined ethereal extracts are washed with water and brine, and concentrated to yield ethyl pregn-3,5,17(20)-triene-3-phosphono-21-oate.

EXAMPLE 16

Androst-3,5,16-triene-17-(N,N-diisopropyl-carboxamide)-3-phosphonic acid

(i)

Androst-3,5,16-triene-17-(trifluoromethyl-sulfonate)-3-phosphonic acid

To a solution of androst-3,5-diene-17-one-3-phosphonic acid (314 mg, 1 mmol), prepared as in Example 14, in 10 ml methylene chloride is added 2,6-di-t-butyl-4-methylpyridine (272 mg, 1.5 mmol) and trifluoromethanesulfonic anhydride (0.3 ml, 1.6 mmol) and the solution is stirred for 4 hours. The reaction mixture is then diluted with methylene chloride, washed with 10% hydrochloric acid, brine, and concentrated to yield crude androst-3,5,16-triene-17-(trifluoromethylsulfonate)-3-phosphonic acid.

(ii)

Androst-3,5,16-triene-17-(N,N-diisopropylcarboxamide)-3-phosphonic acid

A mixture of androst-3,5,16-triene-17-(trifluoromethylsulfonate)-3-phosphonic acid (447 mg, 1 mmol), triethylamine (200 mg, 2 mmol), diisopropylamine (4 g, 40 mmol), and bis(triphenylphosphine)palladium(II) acetate (22 mg, 0.03 mmol) in 4 ml DMF is stirred under an atmosphere of carbon monoxide for 4 hours. The mixture is then diluted with 10% hydrochloric acid and thoroughly washed with dichloromethane. The dichloromethane solution is washed with brine, dried and concentrated, and the residue is recrystallized (diethylether) to yield androst-3,5,16-triene-17-(N,N-diisopropylcarboxamide)-3-phosphonic acid.

EXAMPLE 17

2′,3′α-Tetrahydrofuran-2′-spiro-17-(3,5-androstadiene-3-phosphonic acid

The title compound is prepared according to Example 1 (iii through v) by substituting 2,3′α-tetrahydrofuran-2′-spiro-17-(androst-4-ene-3-one) for androst-4-ene-3-one-17β-N,N-diisopropylcarboxamide.

EXAMPLE 18

17β-Acetamido-3,5-androstadiene-3-phosphonic acid

The title compound is prepared according to Example 1 (iii–iv) by substituting 17β-acetamido-4-androsten-3-one for androst-4-ene-3-one-17β-N,N-diisopropylcarboxamide.

EXAMPLE 19

Androst-3,5-diene-17α-ol-17β-carboxy-3-phosphonic acid

(i) 17β-Cyano-17α-acetoxyandrost-4-ene-3-one

4-Androsten-3,17-dione (20 g) is dissolved by gentle warming in acetone cyanohydrin (30 ml). The crystals which form after several minutes are filtered, washed with pentane, and then dissolved in a mixture of pyridine (50 ml) and acetic anhydride (50 ml). After 48 hours the volatiles are removed under reduced pressure. The residue is then dissolved in ether and washed successively with 5% hydrochloric acid and aqueous sodium bicarbonate. The organic solution is dried and concentrated to afford a mixture of C-17 epimers of 17-cyano-17-acetoxyandrost-4-ene-3-one. Chromatography affords 17β-cyano-17α-acetoxyandrost-4-ene-3-one.

(ii) 17β-cyano-17α-acetoxy-androst-3,5-diene-3-phosphonic acid

The title compound is prepared according to Example 1 (iii–iv) by substituting 17-cyano-17-acetoxy-androst-4-ene-3-one for androst-4-ene-3-one-17β-N,N-diisopropylcarboxamide.

(iii) Androst-3,5-diene-17α-ol-17β-carboxy-3-phosphonic acid

A solution of 3-carbomethoxy-17β-cyano-17α-acetoxyandrost-3,5-diene-3-phosphonic acid in methanol is cooled to 15° C. Dry hydrochloric acid is bubbled into the solution and the mixture allowed to stand at room temperature for 2 hours. Solvent is then removed under reduced pressure. A mixture of 1:1 THF-water is added followed by excess sodium hydroxide and the mixture is stirred for 2 hours. The reaction mixture then is acidified and extracted with chloroform. Concentration of the organic solution affords androst-3,5-diene-17α-ol-17β-phosphonic-3-phosphonic acid which is recrystallized from methanol.

EXAMPLE 20

5α-Androst-3,8(14)-diene-17β-ol-3-phosphonic acid

(i) Androst-5,7-diene-3β,17β-diol

A mixture of androst-5-ene-3β,17β-diol diacetate (3.75 g, 10 mmol), dibromantin (2.03 g, 7 mmol), and sodium bicarbonate (4.54 g, 54 mmol) in hexane (200 ml) is heated under reflux for 0.5 hours. The mixture is then cooled and filtered and the filtrate evaporated to dryness. The residue is dissolved in 50 ml toluene and treated with lithium bromide (2 g) in 5 ml of acetone. The mixture is stirred at 0° C. for 2 hours and then treated with 2 ml triethylamine and 1.5 ml benzenethiol. After stirring at room temperature for 1.5 hours, 100 ml ethyl acetate is added and the organic solution is washed with 1N hydrochloric acid and water. The organic phase is dried and concentrated. The residue is then redissolved in 75 ml ethyl acetate, cooled to 0° C. and treated with 2.6 g of m-chloroperbenzoic acid for 2 hours. The mixture is washed with 10% sodium bicarbonate solution and then concentrated. The residue is dissolved in 100 ml toluene, treated with triethylamine (3.6 ml), heated at 70° C. for 24 hours, cooled, and washed with water. The organic solution was concentrated and chromatographed to yield androst-5,7-diene-3β,17β-diol diacetate. The diacetate is treated with $K_2CO_3$ in a 10:1 methanol:water solution overnight to yield, after extractive workup, androst-5,7-diene-3β,17β-diol.

(ii) Androst-4,7-diene-3,17-dione

A solution of androst-5,7-diene-3β,17β-diol (2.9 g, 10 mmol) in 150 ml toluene is azeotropically dried for one hour. Butanone (15 ml) is added followed by aluminum isopropoxide (1.7 g, 8 mmol) and the mixture is heated at reflux for 2.5 hours. The solution is then concentrated to a volume of 25 ml, diluted with trichloromethane, and washed with 5% hydrochloric acid, aqueous sodium bicarbonate, and brine. Concentration and chromatography affords androst-4,7-diene-3,17-dione.

(iii) 5α-Androst-7-ene-3-one-17β-ol

The title compound is prepared according to the procedure of Example 4 (i) by substituting androst-4,7-diene-3,17-dione for 3-oxo-17β-(hydroxymethyl)-4androstene.

(iv) 5α-Androst-8(14)-ene-3-one-17β-ol

A solution of 5α-androst-7-ene-3-one-17β-ol in ethyl acetate is hydrogenated at room temperature and 1 atmosphere over 10% palladium on carbon for 8 hours. Filtration to remove the catalyst and concentration affords 5α-androst-8(14)-ene-3-one-17β-ol.

(v) 5α-Androst-1,8(14)-diene-3-one-17β-ol

The title compound is prepared according to Example 5 (ii) by substituting 5α-androst-8(14)-ene-3-one-17β-ol for 20α-(hydroxymethyl)-5α-pregnan-3-one.

(vi) 5α-Androst-3,8(14)-diene-17β-ol-3-phosphonic acid

The title compound is prepared according to Example 5 (v through x) by substituting 5α-androst-1,8(14)-diene-3-one-17β-ol for 20α-(hydroxymethyl)-pregn-4-ene-3-one.

EXAMPLE 21

17β-(N,N-Diisopropyl carboxamide)-androst-3,5,7-triene 3-phosphonic acid

(i) Androst-4,6-diene-3-one-17β-N,N-diisopropylcarboxamide

Androst-4-ene-3-one-17β-N,N-diisopropyl-carboxamide (12 g, 30 mmol) and chloranil (8.95 g, 36.4 mmol) in 700 ml t-butanol is heated at reflux for 3.5 hours then cooled and filtered. The filtrate is concentrated and the residue taken up in 700 ml trichloromethane and washed successively with 4×150 ml water, 3×150 ml aqueous sodium bicarbonate, 3×150 ml 5% sodium hydroxide, 3× 150 ml brine, dried over sodium sulfate and concentrated to yield androst-4,6-diene-3-one-17β-N,N-diisopropylcarboxamide.

(ii) 17β-(N,N-Diisopropyl carboxamide)-androst-3,5,7-triene-3-phosphonic acid

The title compound is prepared according to Example 1 (iii-v) by substituting androst-4,6-diene-3-one-17β-N,N-diisopropylcarboxamide for androst-4-ene-3-one-17β-N,N-diisopropylcarboxamide.

EXAMPLE 22

A-Homo-5α-androst-4-ene-17β-N,N-diisopropylcarboxamide-4-phosphonic acid (i)
A-Homo-5α-androstan-4-one-17β-N,N,-diisopropylcarboxamide To a 0° C. solution of 3-oxo-5α-androstane-17β-N,N-diisopropylcarboxamide (15 g), prepared as in Example 4, and KOH (28 g) in ether (500 ml) and methanol (850 ml) is added 20 g of N-methylnitrosourea over 20 minutes. After 5 hours, 300 ml of 10% hydrochloric acid is added and the mixture is filtered and concentrated to remove the organic solvents. The resulting aqueous suspension is extracted with ether and the ethereal solution is dried and concentrated. Chromatography of the residue yields A-homo-5α-androstane-4-one-17β-N,N-diisopropylcarboxamide.

(ii)
A-Homo-5α-androst-4-ene-17β-N,N-diisopropylcarboxamide-4-carboxylic acid

Utilizing the protocol of Example 1 (iii-v), substitution of androst-4-ene-3-one-17β-N,N-diisopropylcarboxamide with A-homo-5α-androstane-4-one-17β-N,N-diisopropylcarboxamide yields a mixture of 3-ene, and 4-ene A-homo-4-phosphonic acids. Chromatography and recrystallization yields pure A-homo-5α- androst-4-ene-17β-N,N-diisopropylcarboxamide-4-phosphonic acid.

EXAMPLE 23

17β-(N,N-Diisopropylcarboxamide)-4-chloro-androst-3,5-diene-3-phosphonic acid (i)
3-Oxo-androstane-4,5α-epoxide-17β-N,N-diisopropylcarboxamide The title compound is prepared according to Example 4 (v) by substituting androst-4-ene-3-one-17β-N,N-diisopropylcarboxamide for 3-oxo-5α-androst-1-ene-17β-N,N-diisopropylcarboxamide.

(ii)
3-Oxo-4-chloro-4-androstene-17β-N,N-diisopropylcarboxamide

A stream of hydrogen chloride gas is passed through a chloroform solution of 3-oxo-androstane-epoxide-17β-N,N-diisopropylcarboxamide for 2 minutes. The solution is then washed with water, dried (Na₂SO₄), and concentrated to yield 3-oxo-4-chloro-4-androstene-17β-N,N-diisopropylcarboxamide.

(iii)
4-Chloro-androst-3,5-diene-17β-N,N-Diisopropyl-carboxamide-3-phosphonic acid The title compound is prepared according to Example 1 (iii through v) by substituting 3-oxo-4-chloro-4-androstene-17β-N,N-diisopropylcarboxamide for androst-4-ene-3-one-17β-N,N-diisopropylcarboxamide.

EXAMPLE 24

17β-(N,N-Diisopropylcarboxamide)-4-methyl-5α-androst-3-ene 3-phosphonic acid (i) 3-Oxo-17β-(hydroxymethyl)-4-methyl-4-androstene A mixture of potassium-t-butoxide (5 g) in 100 ml t-butanol is heated to reflux. A solution of 3-oxo-17β-(hydroxymethyl)-4-androstene (10 g) in t-butanol is added followed by a solution of methyl iodide (2.7 g) in t-butanol. Heating is continued for 3 hours. The mixture is then cooled, acidified, and extracted with dichloromethane. The dichloromethane solution is washed with brine, dried, and concentrated to yield 3oxo-17β-(hydroxymethyl)-4-methyl-4-androstene.

(ii) 17β-(N,N-Diisopropyl carboxamide)-4-methyl-5α-androst-3-ene-3-carboxylic acid The title compound is prepared according to Example 3 (iii through viii) by substituting 3-oxo-17β-(hydroxymethyl)-4-methyl-4-androstene for 3-oxo-17β-(hydroxymethyl)-4-androstene.

EXAMPLE 25

17β-(N,N-Diisopropylcarboxamide)-4-trifluoromethyl-androst-3,5-diene-3-phosphonic acid (i)
3-Oxo-4-trifluoromethyl-4-androstene-17β-N,N-diisopropylcarboxamide A solution of 3-oxo-4-androstene-17β-N,N-diisopropylcarboxamide (1 g) in 10 ml of pyridine is cooled to −78° C. Trifluoromethyl iodide gas is condensed in a dry ice-acetone bath and added to the steroidpyridine cooled solution The resulting solution is photolyzed using a medium pressure 450 watt mercury vapor lamp at room temperature for 18 hours. The reaction mixture is then diluted with ethyl acetate, washed with cold dilute hydrochloric acid, 5% sodium bisulfite, water, brine, dried over anhydrous sodium sulfate, and concentrated to dryness. Purification on a silica gel column eluting with 20% ethyl acetate in hexane yields 3-oxo-4-trifluoromethyl-4-androstene-17β-N,N-diisopropylcarboxamide.

(ii) 17β-(N,N-Diisopropylcarboxamide)-4-trifluoromethyl-androst-3,5-diene-3-carboxylic acid The title compound is prepared according to Example 1 (iii through v) by substituting 3-oxo-4-trifluoromethyl-4-androstene-17β-N,N-diisopropylcarboxamide for androst-4-ene-3-one-17β-N,N-diisopropylcarboxamide.

EXAMPLE 26

17β(N,N-Diisopropylcarboxamide)-6-trifluoromethyl-androst-3,5-diene-3-carboxylic acid

(i) 3-Oxo-6-trifluoromethyl-4-androstene-17β-N,N-diisopropylcarboxamide

17β-N,N-diisopropylcarboxamide-3-(trifluoromethylsulfonate)-androst-3,5-diene (1 g) is dissolved in 10 ml of pyridine and is photolyzed using a Hanovia medium pressure 450 watt mercury vapor lamp at room temperature for 18 hours. The reaction solution is diluted with ethyl acetate which in turn is washed with cold dilute hydrochloric acid, water, brine, dried over anhydrous magnesium sulfate, and evaporated to dryness. Silica gel column chromatography eluting with 20% ethyl acetate in hexane affords 3-oxo-6-trifluoromethyl-4-androsten-17β-N,N-diisopropylcarboxamide.

(ii) 6-Trifluoromethyl-androst-3,5-diene-17β-N,N-diisopropylcarboxamide-3-carboxylic acid The title compound is prepared according to Example 3 (iii through v) by substituting 3-oxo-6-trifluoromethyl-4-androstene-17β-N,N-diisopropylcarboxamide for androst-4-ene-3-one-17β-N,N-diisopropylcarboxamide.

EXAMPLE 27

17β-N,N-Diisopropylcarboxamide-6-fluoro-androst-3,5-diene-3-phosphonic acid

(i) 17β-N,N-Diisopropylcarboxamide-5α-androstene-3-spiro 2'-dioxolane

To a solution of 3-oxo-4-androstene-17β-N,N-diisopropylcarboxamide (8 g) in 300 ml of benzene was added 30 ml of ethylene glycol and p-toluenesulfonic acid (240 mg). The resulting solution was refluxed under argon with water collection using a Dean Stark trap for 30 hours. The reaction mixture was then allowed to cool to room temperature and diluted with ethyl acetate. The organic layer was washed with 5% sodium bicarbonate, brine, dried over anhydrous magnesium sulfate, and evaporated to dryness. The crude material was purified on a silica gel column using 20% ethyl acetate in hexane as the eluting solvent to afford 7 g of 17β-N,N-diisopropylcarboxamide-5α-androstene-3-spiro-2'-dioxolane (80%).

(ii) 17β-(N,N-diisopropylcarboxamide)-5α,6α-epoxy-androstane-3-spiro-2'-dioxolane To a solution of 17β-N,N-diisopropylcarboxamide-5-androstene-3-spiro-2'-dioxolane (4.43 g, 10 mmol) in 100 ml of dry dichloromethane at 0° C. was added a solution of m-chloroperbenzoic acid (2.8 g) in 40 ml of dichloromethane dropwise through a dropping funnel. After completion of addition of m-chloroperbenzoic acid, the reaction mixture was allowed to warm to room temperature and stirred for another 30 minutes. The reaction mixture was then washed with 10% aqueous sodium sulfite solution four times followed by 5% aqueous sodium bicarbonate solution, brine, dried over anhydrous magnesium sulfate, and concentrated to a syrup. Column chromatography, eluting with 30% ethyl acetate in hexane, yielded 2.76 g of 17β-(N,N-diisopropylcarboxamide)-5α,6α-epoxy-androstane-3-spiro-2'-dioxolane as a white solid (61%).

(iii) 3-Oxo-6-fluoro-4-androstene-17β-N,N-diisopropylcarboxamide

17β-(N,N-diisopropylcarboxamide)-5α,6α-epoxy-androstane-3-spiro-2'-dioxolane (2.5 g) was dissolved in a mixture of 50:50 (v/v) benzene and ether. To this solution was added borontrifluoride-etherate (2.5 ml) under argon. The reaction solution was stirred at room temperature under argon for four hours and then quenched with 5% aqueous sodium carbonate. The organic layer was washed with water, brine, dried over anhydrous magnesium sulfate, and evaporated to dryness under reduced pressure. The residue was then treated with 15 ml of saturated hydrogen chloride in glacial acetic acid. The resulting solution was stirred at room temperature under argon for 1.5 hours and then diluted with ethyl acetate. The ethyl acetate solution was washed with 5% aqueous sodium bicarbonate, water, brine, dried over anhydrous magnesium sulfate, and evaporated to dryness. The crude material was purified on a silica gel column eluting with 25% ethyl acetate in hexane to yield 3-oxo-6β-fluoro-4-androstene-17β-N,N-diisopropylcarboxamide (675 mg, 30%) and 3-oxo-6α-fluoro-4-androstene-17β-N,N-diisopropylcarboxamide (900 mg, 40%).

(iv) 17β-(N,N-Diisopropylcarboxamide)-3-(trifluoromethylsulfonate)-6-fluoro-androst-3,5-diene To a solution of the epimers of 3-oxo-6-fluoro-4-androstene-17β-N,N-diisopropylcarboxamide (1.4 9) in 50 ml of dry dichloromethane was added 2,6-di-t-butyl-4-methylpyridine (850 mg) followed by trifluoromethanesulfonic anhydride (0.75 ml) under argon. The resulting solution was stirred at room temperature under argon for 3 hours. The solvent was then removed under reduced pressure. The residue was redissolved in ethyl acetate which in turn was washed with cold dilute hydrochloric acid, water, brine, dried over anhydrous magnesium sulfate, and evaporated to an oil. Column chromatography (silica gel, 10% ethyl acetate in hexane) yielded 17β-N,N-diisopropylcarboxamide-3-(trifluoromethylsulfonate)-6-fluoro-androst-3,5-diene and 17β-N,N-diisopropylcarboxamide-3-(trifluoromethylsulfonate)-6-fluoro-androst-2,4-diene.

(v) Dimethyl 17β-(N,N-diisopropylcarboxamide)-6-fluoro-androst-3,5-diene-3-phosphonate A mixture of 17β-(N,N-diisopropylcarboxamide)-3-(trifluoromethylsulfonate)-6-fluoro-androst-3,5-diene (250 mg), triethylamine (0.12 ml), ethanol (1.5 ml), N,N-dimethylformamide (2 ml) and bis(triphenylphosphine)-palladium(II) acetate (25 mg) is purged with carbon monoxide for 10 minutes. The reaction mixture is stirred under one atmosphere of carbon monoxide at room temperature overnight and then diluted with ethyl acetate. The ethyl acetate solution is then washed with cold dilute hydrochloric acid, water, brine, dried over anhydrous magnesium sulfate, and concentrated to dryness. Silica gel column chromatography eluting with 10% ethyl acetate in hexane gives dimethyl 17β-(N,N-diisopropylcarboxamide)-6-fluoro-androst-3,5-diene-3-phosphonate.

(vi)

17β-(N,N-Diisopropylcarboxamide)-6-fluoro-androst-3,5-diene-3-phosohonic Acid

The title compound is prepared according to Example 3 (viii) by substituting dimethyl 17β-N,N-diisopropylcarboxamide-6-fluoro-androst-3,5-diene-3-phosphonate for 17β-N,N-diisopropylcarboxamide-5α-3-ene-3-phosphonate.

EXAMPLE 28

17β-(N-t-Butylcarboxaide)-androst-3,5-diene-3-phosphonic acid (i) Androst-4-ene-3-one-17β-N-t-butylcarboxamide The title compound was prepared according to Example 1 (ii) by using tert-butylamine in place of diisopropylamine.

(ii) 17β-(N-t-butylcarboxamide)-3-(trifluoromethylsulfonate)-androst-3,5-diene

The title compound was prepared in 45% yield according to Example 1 (iii) by using androst-4-ene-3-one-17β-N-t-butylcarboxamide in place of androst-4-ene-3-one-17β-N,N-diisopropyl carboxamide.

(iii) Dimethyl 17β-(N-t-butylcarboxamide)-androst-3,5-diene-3-phosphonate

The title compound was prepared according to Example 1 (iv) by using 17β-(N-t-butylcarboxamide)-3-(trifluoromethylsulfonate)-androst-3,5-diene in place of 17β-(N,N-diisopropylcarboxamide)- 3-(trifluoromethyl-sulfonate)-androst-3,5-diene.

(iv) 17β-(N-t-Butvlcarboxamide)Androst-3,5-diene-3-ohosohonic Acid

The title compound is prepared according to Example 1(v) by using dimethyl 17β-(N-t-butylcarboxamide)androst-3,5-diene-3-phosphonate in place of dimethyl 17β-(N,N-diisopropylcarboxamide)-androst-3,5-diene-3-phosphonate.

EXAMPLE 29

17β-(N,N-Diisooroovlcarboxamide)-5α-androst-2-ene-3-ohosohonic acid-3-ohosohonic Acid (i) 17β-(N,N-Diisooroovlcarboxamide)-3-(trifluoromethvlsulfonate)-5α-androst-2-ene The title compound is prepared according to Example 4(vii) by using 3-oxo-5α-androstane-17β-N,N-diisopropylcarboxamide in place of 3-oxo-4-fluoro-5α-androst-1-ene-7β-N,N-diisopropylcarboxamide.

(ii) Dimethyl 17β-N,N-diisooroovlcarboxamide-5α-Androst-2-ene-3-phosohonate

The title compound is prepared according to Example 1(iv) by using 17β-(N,N-diisopropylcarboxamide)-3-(trifluoromethylsulfonate)-5α-androst-2-ene in place of 17β-(N,N-diisopropylcarboxamide)-3- (trifluoromethylsulfonate)androst-3,5,-diene.

(iii) 17β-(N,N-Diisooroovlcarboxamide)5α-Androst-2-ene-3-ohosohonic acid

The title compound is prepared according to Example 1(v) by using dimethyl 17β-(N,N-diisopropylcarboxamide)-5α-androst-2-ene-3-phosphonate dimethyl 17β-(N,N-diisopropylcarboxamide)-androst-3,5-diene-3-phosphonate.

EXAMPLE 30

17β-(N,N-Diisopropylcarboxamide)-androst-2,4-diene-ohosohonic acid (i) 17β-(N,N-Diisopropylcarboxamide)-3-trifluoromethylsulfonate)androst-2,4-diene The title compound is prepared according to Example 4(vii) by using 3-oxoandrost-4- ene-17β-N,N-diisopropylcarboxamide in place of 3-oxo-4 fluoro-5α-androst-1-ene-17β-N,N- diisopropylcarboxamide.

(ii) Dimethvl 17β-(N,N-diisooroovlcarboxamide)-androst-2,4-diene-3-phosphonate

The title compound is prepared according to Example 1(iv) by using 17β-(N,N-diisopropylcarboxamide)-3-(trifluoromethylsulfonate)-androst-2,4-diene in place of 17β-(N,N-diisopropylcarboxamide)-3-(trifluoromethylsulfonate)-androst-3,5-diene.

(iii) 17β-(N,N-Diisooroovlcarboxamide)-androst-2,4-diene-3-phosohonic acid

The title compound is prepared according to Example 1(v) by using dimethyl 17β-(N,N-diisopropylcarboxamide androst-2,4-diene-3-phosphate in place of dimethyl 17β-(N,N-diisopropylcarboxamide)-androst-3,5-diene-3-phosphonate.

EXAMPLE 31

17β-(N,N-Diisopropylcarboxamido)-5α-Androstane-17β-3-phosphonic Acid

17β-N,N-diisopropylcarboxamide)-5α-androst-2-ene -3-phosphonic acid (Example 29 (ii) (100 mg) was shaken in a Parr apparatus in 20 mL of a 3:1 solution of ethyl acetate in acetic acid at 25° C. and 1 atm of hydrogen over 30 mg of 10% of palladium on charcoal. The suspension was filtered, the filtrate concentrated and the residue was azeotroped with t-butanol to Yield the title compound.

EXAMPLE 32

17β-(N,N-Diisopropylcarboxamide)-estr-3,5(10)-diene-3-phosohonic acid (i) 3-methoxy-estr-1,3,5(10),16-tetraene-17β-N,N-diisopropylcarboxamide The title compound was prepared according to the two steps of Example 1(iii, iv) by using methyl estrone in place of androst-4-ene-3-one-17β- N,N-diisopropylcarboxamide and diisopropylamine in place of methanol.

(ii) 3-Methoxyestr-1,3,5(10)-triene-17β-N,N-diisopropylcarboxamide

3-Methoxyestr-1,3,5(10),16-tetraene-17β-N,N-diisopropylcarboxamide (4.45g, 11.3 mmol) in 100 ml of a 3:1 solution of ethyl acetate and ethanol was hydrogenated at 25° and 1 atm. over PtO₂ (350 mg) for 6 hours. The solution was filtered to remove the catalyst and concentrated to afford 4.36g (98%) of the title compound.

(iii) 3-Oxoestr-5(10)-ene-17β-N,N-diisporpoyl carboxamide

To a solution of 3-methoxyestrl3,5(10)-triene-17β-N,N-diisopropylcarboxamide (1.4 g, 3.5 mmol) in liquid ammonia (25 ml), THF (10 ml), and t-butanol (10 ml) at −33° C. was added 0.5 g of lithium wire. The solution was stirred for 5 hours and then methanol (10 ml) was slowly added. The ammonia was allowed to evaporate and the residue was then partitioned between water and chloroform. The organic phase was concentrated to a white solid which was suspended in a methanol-water mixture and then treated with 1.4 g oxalic acid for 1.5 hours. The reaction mixture was then diluted with water and extracted with ethyl acetate. The organic phase was concentrated and the residue chromatographed (silica, 1:9 ethyl acetate-hexane) to yield 0.4 g of the title compound.

(iv) 17β-(N,N-Diisopropylcarboxamide)-estr-3,5(10)-diene-3-phosphonic acid

The title compound is prepared according to Example 29, (i-iii), by using 3-oxoestr-5(10)-ene-17β-N,N-diisopropylcarboxamide for 3-oxo-5α-androstane-17β-N,N-diisopropylcarboxamide.

EXAMPLE 33

17β-(N,N-Diisopropylcarboxamide-estr-3,5-diene-3-phosphonic acid (i) 3-Oxoestr-4-ene-17β-N,N-diisopropylcarboxamide 3-Oxoestr-5(10)-ene-17β-N,N-diisopropylcarboxamide (Example 32, (iii)) is dissolved in methanol and 10% aqueous HCl (2:1) and heated at 65° for 1 hour, cooled, and thoroughly extracted with chloroform. The organic extracts are concentrated to yield the title compound as a white solid.

(ii) 17β-(N,N-Diisopropylcarboxamide)-estr-3,5-diene-3-phosphonic acid

The title compound was prepared according to Example 1(iii-v) by using 3-oxo-estr-4- ene-17β-N,N-diisopropylcarboxamine in place of androst-4-ene-3-one-17β-N,N-diisopropylcarboxamide.

EXAMPLE 34

17β-(N,N-Diisopropylcarboxamide)-Androst-3,5,11-triene-3-phosphonic Acid (i) Androst-4-ene-3-one-11-ol-17β-carboxylic Acid Carticosterone is dissolved in methanol and treated with an aqueous solution of acid at room temperature for 18 hours. The solution is then diluted with water to induce precipitation of androst-4-ene-3-one-11-ol-17β-carboxylic acid which is collected by filtration.

(ii) Androst-4-ene-3,11-diene-17β-carboxylic Acid

To a solution of androst-4-ene-3-one-11-ol-17β-carboxylic acid in acetone is added Jones Reagent to quench the excess oxidant. The solution is decanted and the residual chromium salts are thoroughly washed with acetone. The combined organic solutions are then filtered through magnesium sulfate and concentrated to yield androst-4-ene-3,11-dione-17β-carboxylic acid.

(iii) Androst-4-ene-3,11-dione-17β-(N,N-diisopropylcarboxamide).

The title compound is prepared according to Example 1 (ii) by substituting androst-4-ene-3-one-17β-carboxylic acid.

(iv) 17β-(N,N-Diisopropylcarboxamide)-3-(trifluoromethylsulfonate)-11-oxo-androst-3,5-diene.

The title compound is prepared according to Example 1 (iii) by substituting androst-4-ene-3,11-dione-17β-(N,N-diisopropylcarboxamide) for androst-4-ene-3-one-17β-(N,N,-diisopropylcarboxamide).

(v) Dimethyl 17β-(N,N-22-oxo-androst-3,5-diene-3-phosphonate-diisopropylcarboxamide).

The title compound is prepared according to Example 1 (iv) by substituting 17β-(N,N-diisopropylcarboxamide)-3-trifluoromethylsulfonate)-11-oxo-androst-3,5-diene for 17β-(N,N-diisopropyl-carboxamide)-3-(trifluoromethylsulfonate)-androst-3,5-diene.

(vi) Dimethyl 17β-(N,N-diisopropylcarboxamide)-11-(trifluoromethylsulfonate)-androst-3,5,11-triene-3-phosohonate.

The title compound is prepared according to Example 4(vi) by substituting the compound (v) of this example for 3-oxo-4-fluoro-5α-androst-1-ene-17β-(N,N-diisopropyl-carboxamide.

(vii) Dimethyl 17β-(N,N-diisopropylcarboxamide)-androst 3,5,11-triene 3 phosphonate The title compound is prepared according to the procedure of Cacchi (Tet. Lett. 25 (42) 4821–4824 (1984)) by substituting dimethyl 17β-(N,N-diisopropylcarboxamide)-11-(trifluoromethylsulfonate)-androst 3,5,11 triene-3phosphonate for 17β-acetoxyandrosta-3,5 diene 3 -yl triflate.

(viii) 17β-(N,N-Diisopropylcarboxamide)-androst 3,5,11 triene 3-phosphonic Acid

The title compound is prepared according Example 1(v) by substituting dimethyl 17β-(N,N-diisopropylcarboxamide) androst-3,5,11-triene 3-phosphonate for 17β-(N,N diisopropylcarboxamide) androst 3,5-diene 3-phosphonate. The title compound is a white solid; m.p. 235°–240° C.

EXAMPLE 35

17β-(N-t-Butylcarboxamide)-androst 3,5,11 triene-3-phosphonate acid

The process of Example 34 wherein N-t-butylamine is used in place o diisopropylamine in procedure of Example 1 (ii) yields 17β-N-t-butylcarboxamide)-androst-3,5,11 triene 3-phosphonic acid.

EXAMPLE 36

Monomethyl 17β-(N,N diisopropylcarboxamide)-androst-3,5 diene-3-phosphonate

A solution of 50 mg (0.1 mmole) of dimethyl 17β-(N,N-diisopropylcarboxamide)-androst-3,5-diene-3-phosphonate in 10 mL of 10:1 methanol/water was treated with 10 mg of potassium carbonate and then refluxed under an atmosphere of argon for 17 hours. The reaction was concentrated in vacuo, acidified with dilute HCa and the aqueous layer was extracted repeatedly with methylene chloride. The combined organic extracts were dried (Na$_2$SO$_4$), concentrated and the residue was crystallized from methanol/water to afford monomethyl 17β-N,N-diisopropylcarboxamido-androst-3,5-diene-3-phosphonate; m.p. 212°–215° C.

EXAMPLE 37–46

The following compounds are prepared by substituting t-butylamine for diisopropylamine using the procedure of examples 1, 3 (3a), 4, 7, 27, 29, 30, 31, 32, and 33, respectively:

37. 17β-(N-t-butylcarboxamide)-androst-3,5-diene-3-phosphonic acid precipitated from acetone-diethyl ether-hexane);
38. 17β-(N-t-butylcarboxamide)-5α-androst-3-ene-3-phosphonic acid;
39. 17β-(N-t-butylcarboxamide)-4-fluro-5α-androst-3-ene-3-phosphonic acid;
40. 17β-(N-t-butylcarboxamide)-5α-androst-1,3-diene-3-phosphonic acid;
41. 17β-(N-t-butylcarboxamice)-6-fluoro-androst-3,5-diene-3-phosphonic acid;
42. 17β-(N-t-butylcarboxamide)-5α-androst-2-ene-3-phosphonic acid;
43. 17β-(N-t-butylcarboxamide)-androst-2,4-diene-3-phosphonic acid;
44. 17β-(N-t-butylcarboxamide)-5α-androstane-3-phosphonic acid;
45. 17β-(N-t-butylcarboxamide)-estr-3,5(10)-diene-3-phosphonic acid; and
46. 17β-(N-t-butylcarboxamide)-estr-3,5-diene-3-phosphonic acid.

EXAMPLE 47

17β-N,N-diisopropylcarboxamide-5α-androst-3,8(14)-diene-3-phosphonic acid

The title compound is prepared according to Example 4 (viii-x) by substituting 17β-(N,N-diisopropylcarboxamide)-3-trifluoromethylsulfonate-5α-androst-1,3,8(14)-triene in place of 17β-(N,N-diisopropylcarboxamido)-3-trifluoromethylsulfonate-4-fluoro-5α-androst-1,3-diene.

EXAMPLE 48

An oral dosage form for administering Formula (I) compounds is produced by screening, mixing, and filling into hard gelatin capsules the ingredients in the proportions shown in Table V, below.

TABLE V

| INGREDIENTS | AMOUNTS |
| --- | --- |
| 17β-N,N-diisopropylcarboxamide)-androst-3,5-diene-3-phosphonic acid | 50 mg |
| magnesium stearate | 5 mg |

TABLE V-continued

| INGREDIENTS | AMOUNTS |
| --- | --- |
| lactose | 75 mg |

EXAMPLE 49

The sucrose, calcium sulfate dihydrate and Formula (I) compound shown in Table VI below, are mixed and granulated in the proportions shown with 10% gelatin solution. The wet granules are screened, dried, mixed with the starch, talc and stearic acid, screened and compressed into a tablet.

TABLE VI

| Ingredients | Amounts |
| --- | --- |
| 17β-(N,N-diisopropylcarboxamide)-5α-androst-3-ene-phosphonic acid | 100 mg |
| calcium sulfate dihydrate | 150 mg |
| sucrose | 20 mg |
| starch | 10 mg |
| talc | 5 mg |
| stearic acid | 3 mg |

EXAMPLE 50

17β-(N,N-diisopropylcarboxamide-3,5-diene-3-phosphonic acid 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the formula:

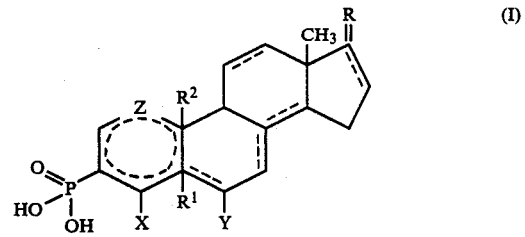

in which the A ring has up to 2 double bonds;
the B, C, and D rings have optional double bonds where indicated by the broken lines, provided that the A B and C ring does not have adjacent double bonds and the D ring does not have a $C_{16}$–$C_{17}$ double bond when R represents two substituents or a divalent substituent;
Z is $CH_2$ or, when part of a double bond, CH;
X is H, Cl, F, Br, I, $CF_3$, or $C_{1-6}$alkyl;
Y is H, $CF_3$, F, or Cl, $CH_3$, provided that Y is H when there is no $C_5$–$C_6$ double bond;
$R^1$ is absent or present as an alpha hydrogen, provided $R^1$ is absent when there is a $C_4$–$C_5$, $C_5$–$C_6$, or $C_5$–$C_{10}$ double bond;
$R^2$ is absent or present as H or $CH_3$ provided $R^2$ is absent when the carbon to which it is attached is double bonded, and
R is
(1) α-hydrogen, α-hydroxyl, or α-acetoxy and/or

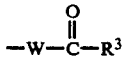
 (a)

where W is a bond or C$_{1-12}$alkyl, and R$^3$ is
(i) hydrogen,
(ii) hydroxyl,
(iii) C$_{1-8}$alkyl,
(iv) hydroxy C$_{1-8}$alkyl,
(v) C$_{1-8}$alkoxy,
(vi) N(R$^4$)$_2$, where each R$^4$ is independently selected from hydrogen, C$_{1-8}$alkyl, C$_{3-6}$cycloalkyl, phenyl; or taken together with the nitrogen to which they are attached represent a 5–6 membered saturated ring comprising up to one other heteroatom selected from oxygen and nitrogen, or
(vii) OR$^5$, where R$^5$ is hydrogen, alkali metal, C$_{1-18}$alkyl, benzyl, or
(b) —Alk-OR$^6$, where Alk is C$_{1-12}$alkyl, and R$^6$ is
(i) phenylC$_{1-6}$alkylcarbonyl,
(ii) C$_{5-10}$cycloalkylcarbonyl,
(iii) benzoyl,
(iv) C$_{1-8}$alkoxycarbonyl,
(v) aminocarbonyl, or C$_{1-8}$alkyl substituted aminocarbonyl,
(vi) hydrogen, or
(vii) C$_{1-8}$alkyl,
(2) =CH—W—CO—R$^3$ or =CH—W—OR$^6$, where W is a bond or C$_{1-12}$alkylidene, and R$^3$ and R$^6$ have the same meaning as above and R$^6$ also is hydrogen or C$_{1-20}$-alkylcarbonyl;

 (3)

where the dashed bond replaces the 17α-hydrogen,
(4) α-hydrogen and NHCOR$^7$ where R$^7$ is C$_{1-12}$alkyl or N(R$^4$)$_2$ where R$^4$ has the same meaning as above,
(5) α-hydrogen and cyano,
(6) α-hydrogen and tetrazolyl, or
(7) keto;
or a pharmaceutically acceptable salt thereof.

2. A compound of claim 1 having the following formula:

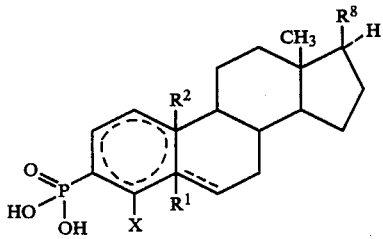 II in which
the A ring has up to 2 double bonds;
the B ring has an optional double bond where indicated by the broken line and provided that the A and B rings do not have adjacent double bonds;
X is H or halo, and
R$^1$ is absent or present as an alpha hydrogen provided R$^1$ is absent when there is a C$_4$–C$_5$, C$_5$–C$_6$, or C$_5$–C$_{10}$ double bond, and R$^8$ is
(a) C(CH$_3$)CH$_2$OR$^9$ wherein R$^9$ is H or C$_{1-6}$alkyl, or
(b) CON(R$^9$)$_2$ wherein each R$^9$ independently is H or C$_{1-8}$alkyl or a pharmaceutically acceptable salt thereof.

3. A compound of claim 2 wherein a ring has a C$_3$–C$_4$ double bond.

4. The compound of claim 2 that is 17β-(N,N-diisopropylcarboxamide)-androst-3,5-diene-phosphonic acid or a pharmaceutically acceptable salt thereof.

5. The compound of claim 2 that is 17β-(N,N-diisopropylcarboxamide)-5α-androst--3-ene-3-phosphonic acid or a pharmaceutically acceptable salt thereof.

6. The compound of claim 2 that is 17β-(N-t-butylcarboxamide)-androst-3,5-diene-3-phosphonic acid or a pharmaceutically acceptable salt thereof.

7. The compound of claim 2 that is 17β-(N,N-diisopropylcarboxamide)-androst-2-phosphonic acid or a pharmaceutically acceptable salt thereof.

8. The compound of claim 2 that is 17β-(N,N-diisopropylcarboxamide)-androst-2,4-diene-3-phosphonic acid or a pharmaceutically acceptable salt thereof.

9. A pharmaceutical composition comprising a compound of claim 1 and a pharmaceutically acceptable carrier.

10. A composition of claim 9 wherein the compound is 17β-(N,N-diisopropylcarboxamide)-androst-3,5-diene-3-phosphonic acid or a pharmaceutically acceptable salt thereof.

11. A composition of claim 9 wherein the compound is 17β-(N-t-butylcarboxamide)-androst-3,5-diene-3-phosphonic acid or a pharmaceutically acceptable salt thereof.

12. A composition of claim 9 wherein the compound is 17β-(N,N-diisopropylcarboxamide)-5α-androst-3-ene-3-phosphonic acid or a pharmaceutically acceptable salt thereof.

13. A composition of claim 9 wherein the compound is 17β-(N,N-diisopropylcarboxamide)-androst-2-ene-3-phosphonic acid or a pharmaceutically acceptable salt thereof.

14. A composition of claim 9 wherein the compound is 17β-(N,N-diisopropylcarboxamide)-androst-2,4-diene-3-phosphonic acid or a pharmaceutically acceptable salt thereof.

15. A method of inhibiting steroid 5α-reductase activity in mammals that comprises administering to a subject an effective amount of a compound of claim 1.

16. A method of claim 15 wherein the compound is 17β-(N,N diisopropylcarboxamide)-androst-3,5,diene-3-phosphonic acid or a pharmaceutically acceptable salt thereof.

17. A method of reducing or maintaining prostate size in a manner that comprises administering to a subject an effective amount of a compound of claim 1.

18. The compound represented by the formula:

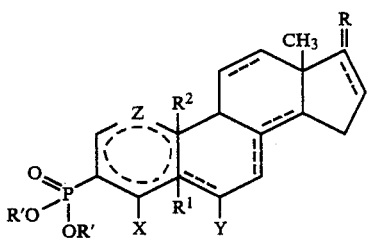

in which:

the A ring has up to 2 double bonds;

the B, C, and D rings have optional double bonds where indicated by the broken lines, provided that the A, B and C rings do not have adjacent double bonds and the D ring does not have a $C_{16}$–$C_{17}$ double bond when R represents two substituents or a divalent substituent;

Z is $CH_2$ or, when part of a double bond, CH;

X is H, Cl, F, Br, I, $CF_3$, or $C_{1-6}$alkyl;

Y is H, $CF_3$, F, Cl or $CH_3$, provided that Y is H when there is no $C_5$–$C_6$ double bond;

one R' is $C_{1-8}$alkyl and the other R' is hydrogen or $C_{1-8}$alkyl;

$R^2$ is absent or present as H or $CH_3$, provided $R^2$ is absent when the carbon to which it is attached is double bonded; and $R^1$ is absent or present as an alpha hydrogen provided $R^1$ is absent when there is a $C_4$–$C_5$, $C_5$–$C_6$, or $C_5$–$C_{10}$ double bond; and R is (1) α-hydrogen, α-hydroxyl, or α-acetoxy and/or

     (a)

where W is a bond or $C_{1-12}$alkyl and $R^3$ is (i) hydrogen,
(ii) hydroxyl,
(iii) $C_{1-8}$alkyl,
(iv) hydroxy $C_{1-8}$alkyl,
(v) $C_{1-8}$alkoxy,
(vi) $N(R^4)_2$, where each $R^4$ independently selected from hydrogen, $C_{1-8}$alkyl, $C_{3-6}$cycloalkyl, phenyl; or taken together with the nitrogen to which they are attached represent a 5–6 membered saturated ring comprising up to one other heteroatom selected from oxygen and nitrogen, or
(vii) $OR^5$, where $R^5$ is hydrogen, alkali metal, $C_{1-18}$alkyl, benzyl, or (b) —Alk—$OR^6$, where Alk is $C_{1-12}$alkyl, and $R^6$ is (i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) aminocarbonyl, or $C_{1-8}$alkyl substituted aminocarbonyl,
(vi) hydrogen, or
(vii) $C_{1-8}$alkyl, (2) =CH—W—CO—$R^3$ or =CH—W—$OR^6$, where W is a bond or $C_{1-12}$alkylidene, and $R^3$ and $R^6$ have the same meaning as above and $R^6$ also is hydrogen or $C_{1-20}$alkylcarbonyl;

     (3)

where the dashed bond replaces the 17β-hydrogen, (4) α-hydrogen and $NHCOR^7$ where $R^7$ is $C_{1-12}$alkyl or $N(R^4)_2$ where $R^4$ has the same meaning as above, (5) α-hydrogen and cyano, (6) α-hydrogen and tetrazolyl, or (7) keto;

or a pharmaceutically acceptable salt thereof.

19. A compound of claim 18 wherein R' is methyl.

20. A compound of claim 18 wherein one R' is methyl and the other R is hydrogen.

21. A process for preparing compounds of the formula:

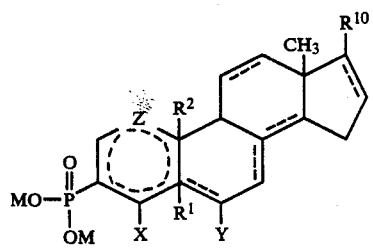

in which:

the A ring has up to 2 double bonds;

the B, C, and D rings have optional double bonds where indicated by the broken lines, provided that the A, B and C rings do not have adjacent double bonds and the D rings does not have a $C_{16}$–$C_{17}$double bond when $R^{10}$represents two substituents or a divalent substituent;

M is $C_{1-8}$alkyl;

Z is $CH_2$ or, when part of a double bond, CH;

X is H, Cl, F, Br, I, $CF_3$, or $C_{1-6}$alkyl;

Y is H, $CF_3$, F, or Cl, $CH_3$, provided that Y is H when there is no $C_5$–$C_6$ double bond;

$R^1$ is absent or present as an alpha hydrogen produced $R^1$ is absent when there is a $C_4$–$C_5$, $C_5$–$C_6$, or $C_5$–$C_{10}$ double bond; and $R^2$ is absent or present as H or $CH_3$, provided $R^2$ is absent when the carbon to which is attached is double bonded; are $R^{10}$ is (1) α-hydrogen, α-hydroxyl, or α-acetoxy and/or

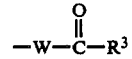     (a)

where w is a bond or $C_{1-12}$alkyl and $R^3$ is (i) hydrogen,
(ii) hydroxyl,
(iii) $C_{1-8}$alkyl,
(iv) hydroxy $C_{1-8}$alkyl,
(v) $C_{1-8}$alkoxy,
(vi) $N(R^4)_2$, where each $R^4$ is independently selected from hydrogen, $C_{1-8}$alkyl, $C_{3-6}$cycloalkyl, phenyl; or taken together with the nitrogen to which they are attached represent a 5–6 membered saturated ring comprising up to one other heteroatom selected from oxygen and nitrogen, or
(vii) $OR^5$, where $R^5$ is hydrogen, alkali metal, $C_{1-18}$alkyl, benzyl, or (b) —Alk—$OR^6$, where Alk is $C_{1-12}$alkyl, and $R^6$ is (i) phenyl $C_{1-6}$alkylcarbonyl,
(ii) $C_{5-10}$cycloalkylcarbonyl,
(iii) benzoyl,
(iv) $C_{1-8}$alkoxycarbonyl,
(v) amino, or $C_{1-8}$alkyl substituted amino, carbonyl,
(vi) hydrogen, or
(vii) $C_{1-8}$alkyl, (2) =CH—W—CO—$R^3$ or =CH—W—$OR^6$, where W is a bond or $C_{1-12}$alkylidene, and $R^3$ and $R^6$ have the same meaning as above and $R^6$ also is hydrogen or $C_{1-20}$alkylcarbonyl;

where the dashed bond replaces the 17α-hydrogen, (4) α-hydrogen and NHCOR⁷ where R⁷ is $C_{1-12}$alkyl or $N(R^4)_2$ where $R^4$ has the same meaning as above, (5) α-hydrogen and cyano, (6) α-hydrogen and tetrazolyl, or (7) keto; or (8) moieties which can be chemically converted to moieties (1) through (7) above;

or a pharmaceutically acceptable salt thereof which process comprises: reacting a compound of the Formula:

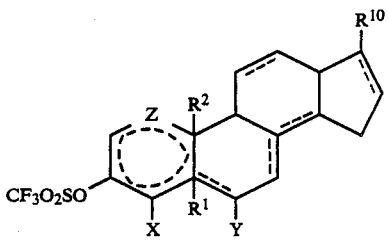

wherein the substituents are as defined above with a posphite and a palladium catalyst in a non-reactive organic solvent to give a 3-phosphonate compound of Formula I; and thereafter optionally forming a pharmaceutically acceptable salt.

22. The process of claim 21 wherein the compound prepared is dimethyl 17β-(N,N-diisopropylcarboxamide)-androse-3,5-diene-3-phosphonate.

23. The process of claim 21 wherein the compound prepared is dimethyl 17β-(N-t-butylcarboxamide)-androst-3,5-diene 3-phosphonate.

24. A process according to claim 21 wherein the palladium catalyst is tetrakis (triphenylphosphine)palladium and the phosphite complex is dimethylphosphite.

* * * * *

UNITED STATES PATENT AND TRADEMARK OFFICE
CERTIFICATE OF CORRECTION

PATENT NO. : 4,946,834

DATED : August 7, 1990

INVENTOR(S) : Dennis A. Holt, Mark A. Levy, Brian W. Metcalf

It is certified that error appears in the above-identified patent and that said Letters Patent is hereby corrected as shown below:

Claim 21, column 50, line 22;
delete "D rings" and replace with --- D ring ---.

Claim 21, column 50, line 35:
delete "are" and replace with --- and ---.

Claim 22, column 52, line 19:
delete "androse" and replace with --- androst ---.

Signed and Sealed this

Twelfth Day of November, 1991

Attest:

HARRY F. MANBECK, JR.

*Attesting Officer*     *Commissioner of Patents and Trademarks*